United States Patent [19]
Pang et al.

[11] Patent Number: 6,156,291
[45] Date of Patent: *Dec. 5, 2000

[54] CHEMICAL AND PHARMACOLOGICAL STANDARDIZATION OF HERBAL EXTRACTS

[75] Inventors: Peter K. T. Pang, Sherwood Park; Jacqueline J. Shan; Kam Wai Chiu, both of Edmonton, all of Canada

[73] Assignee: CV Technologies Inc., Edmonton, Canada

[ * ] Notice: This patent issued on a continued prosecution application filed under 37 CFR 1.53(d), and is subject to the twenty year patent term provisions of 35 U.S.C. 154(a)(2).

[21] Appl. No.: 09/143,361

[22] Filed: Aug. 28, 1998

Related U.S. Application Data

[60] Provisional application No. 60/056,092, Aug. 28, 1997.
[51] Int. Cl.$^7$ ............................. A01N 65/00; A61K 49/00; A61K 35/78
[52] U.S. Cl. ............................. 424/9.2; 424/9.1; 424/195.1
[58] Field of Search ................................. 424/195.1, 9.1, 424/9.2

[56] References Cited

U.S. PATENT DOCUMENTS

| | | | |
|---|---|---|---|
| 5,547,674 | 8/1996 | Khwaja | 424/195.1 |
| 5,780,037 | 7/1998 | Khwaja | 424/195.1 |
| 6,039,950 | 3/2000 | Khwaja | 424/195.1 |

*Primary Examiner*—Herbert J. Lilling
*Attorney, Agent, or Firm*—Arent Fox Kintner Plotkin & Kahn, PLLC

[57] ABSTRACT

One of the aspects of the present invention relates to a method of obtaining a reproducible extraction process for use as a standard process for extracting a pharmacologically active mixture of chemical components from a plant, the method comprising:

(a) extracting a plurality of pharmacologically active mixtures of chemical components from the plant in a plurality of different extraction processes to obtain a plurality of extracts;

(b) obtaining a biological fingerprint of the pharmacological activity of each extract from step (a) by conducting at least two in vitro and at least two in vivo pharmacological tests on each extract, wherein each of the tests is known to correlate with effective treatment of a medical condition in a patient;

(c) choosing one of the plurality of extracts which displays the best pharmacological activity in step (b);

(d) repeating, at least once, the extraction process used to produce the chosen extract of step (c) to produce at least one test extract;

(e) (1) obtaining chemical fingerprints of the chosen extract and the at least one test extract by distinguishing the identity and amount, relative to each other, of the chemical components in the pharmacologically active mixture of each extract, and
(2) repeating said step (b) using the at least one test extract; and (f) comparing the chemical fingerprints and the biological fingerprints of the chosen extract and the at least one test extract.

8 Claims, 29 Drawing Sheets

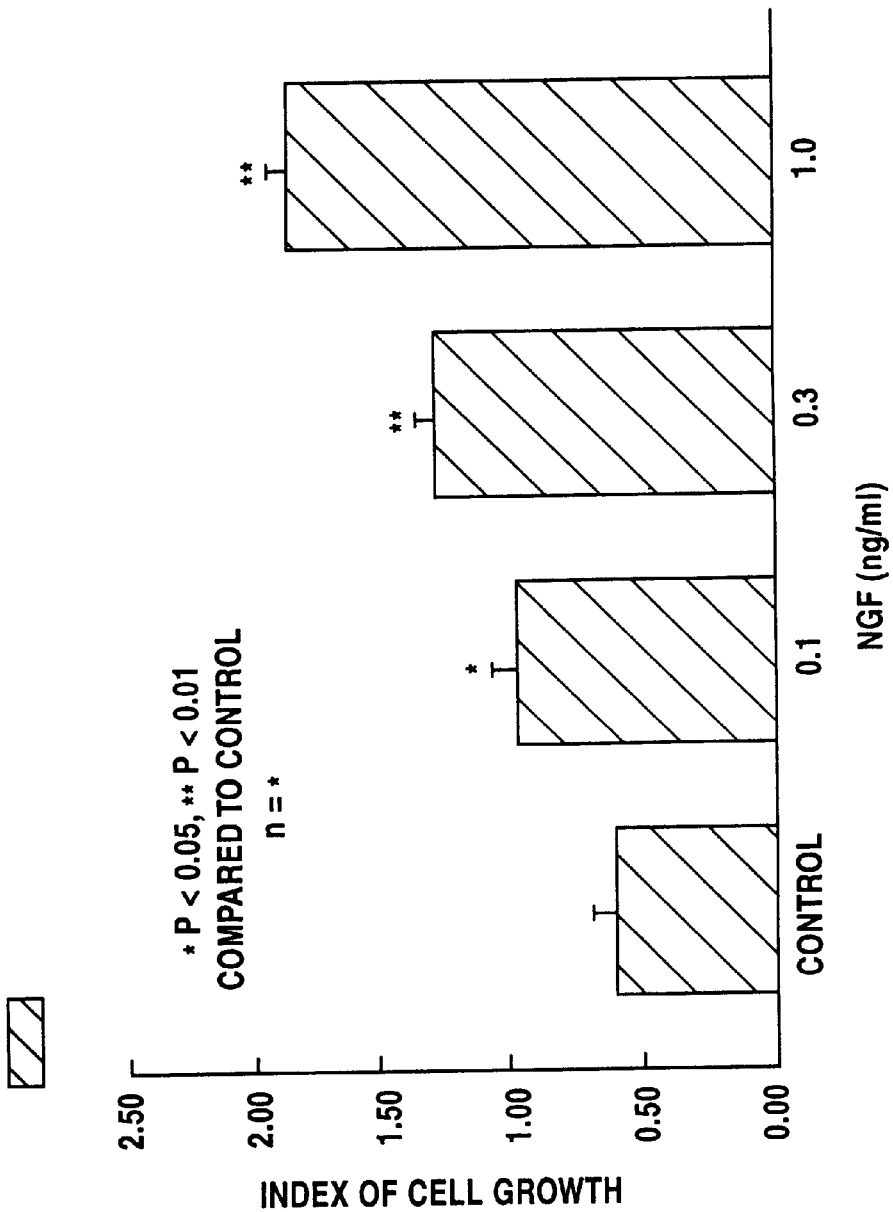

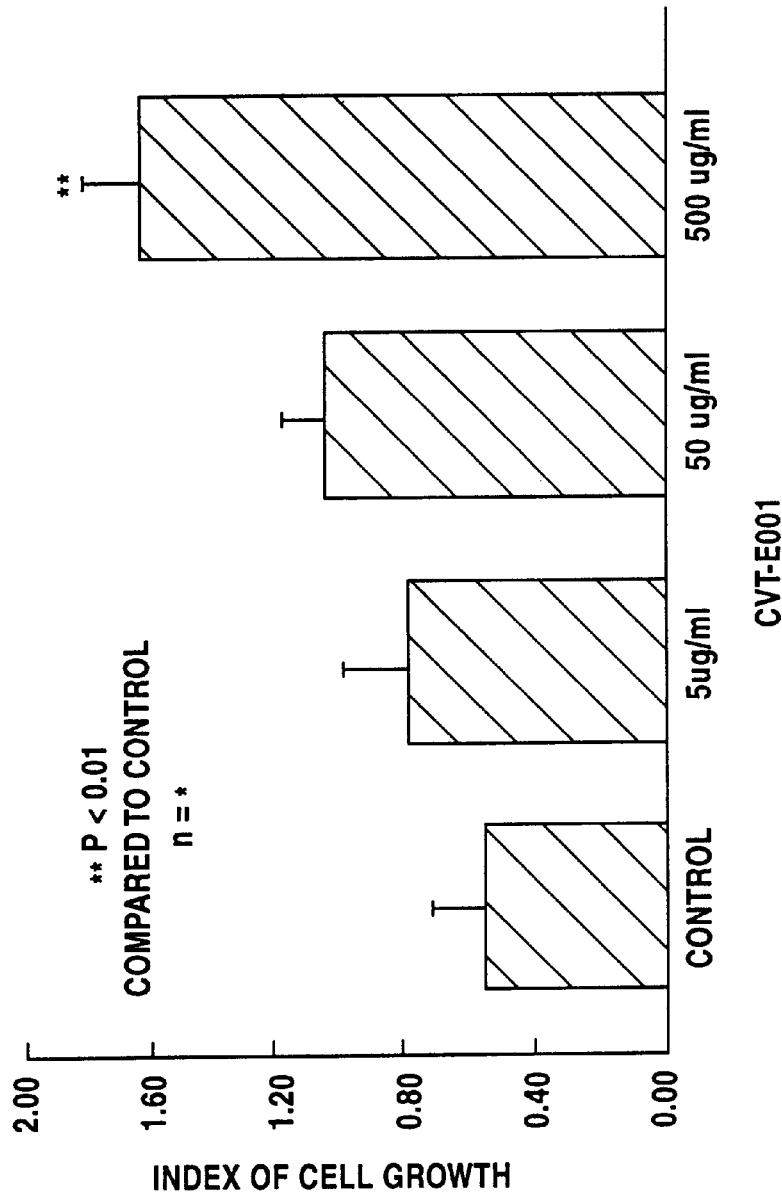

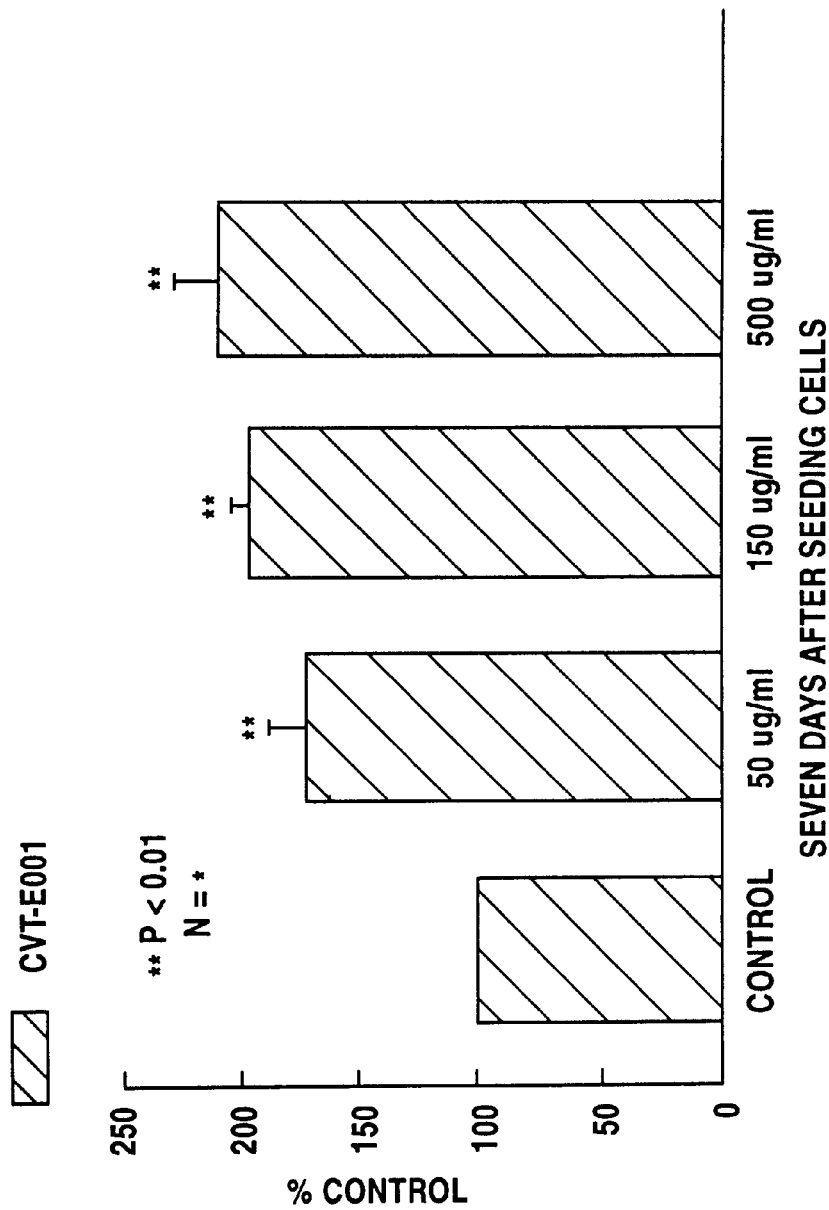

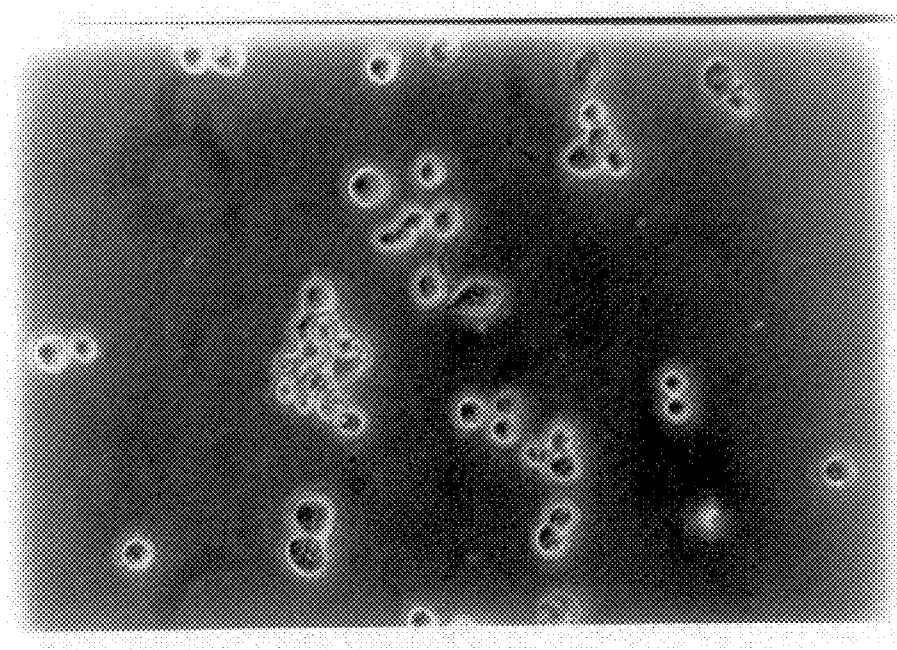
Fig. 29　　CONTROL
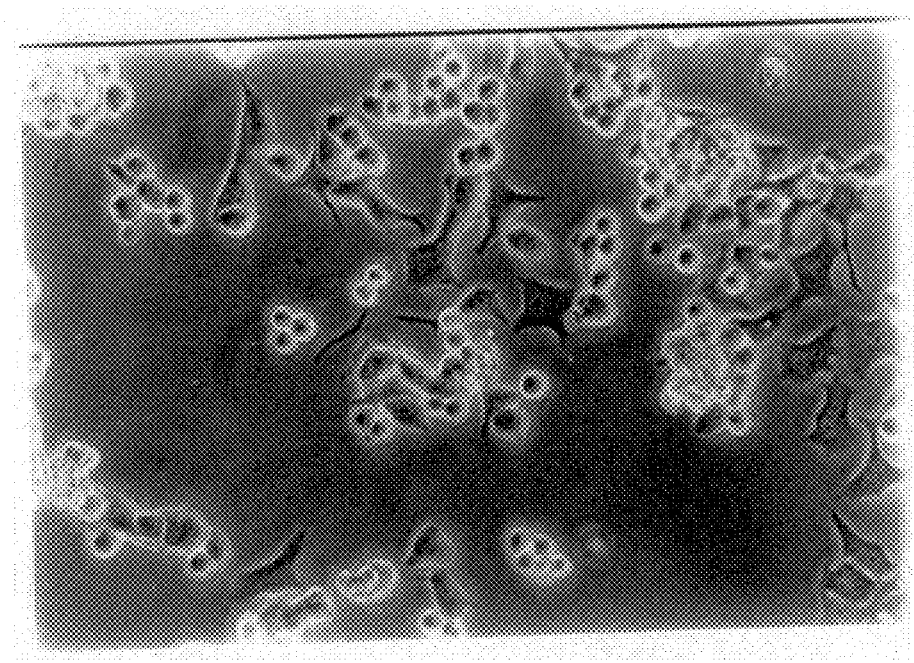
Fig. 30　　HT 150

CHEMICAL AND PHARMACOLOGICAL STANDARDIZATION OF HERBAL EXTRACTS

This application claims the benefit of U.S. Provisional Application No. 60/056,092, filed Aug. 28, 1997.

TECHNICAL FIELD

This invention is directed to a method of assuring reproducibility of an extraction process. The present invention is also directed to a method of reproducibly extracting a pharmacologically active mixture of chemical components from a biological source, particularly a plant source. Furthermore, the present invention is directed to a method of obtaining a pharmacologically active mixture obtained from a biological source having a high pharmacological activity.

BACKGROUND ART

In addition to their herbs common use in cooking, herbs have been used in herbal treatments and herbal medicine since shortly after the beginning of human culture. Herbs have also been used as dietary additives to enhance daily activity in certain cultures. Typically herbs used in such treatments and as dietary additives are ingested as an infusion or tea, or are applied externally as a poultice. In such applications, the herbs employed are typically mixtures of many chemical compounds. Generally, the proper use of widely accepted herbal treatments does not give rise to adverse side effects in a patient. Although the effectiveness of herbal treatments is firmly established in those cultures which have employed such treatments for centuries, it has not yet been "legitimized" in Western scientific documentation.

Western pharmaceuticals are generally employed as either single compounds or mixtures of relatively few compounds administrated either alone or, more preferably, in a pharmaceutically acceptable carrier. The research and development of these single compounds as drugs is in large part due to the creation of strong scientific and clinical documentation. Unfortunately, many of these drugs have a relatively short history of use and many have been shown to produce serious side effects.

Although to some extent a generalization, Western pharmaceutical expression could be considered as a science of healing, while traditional herbal medicine may be viewed as the art of healing. In modern day, herbal medicine, although gaining some acceptance in Western society, still faces several specific challenges. First, in the opinion of many highly trained medical practitioners there is the view that herbal medicine lacks sufficient scientific support data in our highly technical and science-oriented society. Secondly, there is concern about which components of an herbal remedy are pharmaceutically effective. Furthermore, the question arises as to the concentrations or dosages present of such pharmaceutically effective components of herbal remedies. In short, traditional medical practitioners are concerned with a lack of both qualitative and quantitative standards for herbal medications. Such a lack of standardization is viewed as hindering the ability to prescribe and adjust dosages of such nontraditional or herbal medications. The lack of such standardization has also lead to a reluctance on the part of regulatory agencies in further investigating and acceptance of such nontraditional medications.

Although not meeting some of the criteria of Western traditional medicine, such herbal compositions are known to be quite effective in treatment of a variety of maladies with little or no side effects. In part, the pharmaceutical activity in many instances is attributable not only to the presence of specific biologically active compounds but also to a synergistic effect resulting from the combination of two or more chemical components present in the herbal mixture.

Since herbal treatments, defined as both herbal medications and biologically enhancing herbal compositions, are derived from plants, the chemical composition of such herbal treatments varies according to a number of factors, not the least of which are the genetic composition and growing conditions in which the plant is produced as well as the harvest conditions and isolation of the active components of the plant. Accordingly, biological variants of a particular plant may typically be expected to produce significant variations in quantities of particular chemical components found in the plant. Likewise, even in the same biological variant of a plant, differences in soil, moisture and other growing conditions may significantly affect the quantities of specific chemical components produced by the plant.

Finally, the manner in which a plant is processed can drastically influence the relatively proportions and total amounts of specific chemical components isolated from the plant. Thus, such steps as harvesting, storage, reduction in particle size, expression of liquid components and extraction all determine the proportions and amounts of chemical components and hence the pharmaceutical activity of the isolated product.

Considering the many factors which influence the composition and pharmaceutical activity of herbal compositions, it is desirable to employ methods which result in the standardization of herbal compositions both with respect to the chemical compositions thereof and the pharmaceutical activity of such chemical mixtures. In addition, although it may be impossible to standardize growing conditions of plants grown on a large scale, it is desirable to standardize processing conditions in order to obtain such standardized herbal compositions. Furthermore, being able to accurately determine and compare the compositions of biological mixtures, particularly plant or herbal mixtures, would allow processing conditions to be controlled to obtain high pharmacological activity. With such methods available to the scientific community, not only would physicians be able to prescribe specified dosages of herbal compositions with confidence, but herbal composition "manufacturers" would achieve higher pharmaceutical activity of such mixtures, improved quality control and the ability to differentiate herbal mixtures from varying sources.

DISCLOSURE OF INVENTION

The present invention provides both a method of obtaining standardized biological compositions having high pharmaceutical activity and to a method of obtaining standardized processing procedures. The present invention also permits the isolation of biological compositions, and in particular herbal compositions, having high, or the highest pharmacological activity obtainable by a specific process, such as extraction. Herein, a "biological composition", refers to a mixture of components obtained from a biological source. Such source may be either an animal or plant. The present invention is expected to have most widespread application to plant or vegetable sources. The term "composition", as used herein, refers to a mixture of components. As used herein, "components" refers to chemical compounds, salts of such compounds, complexes and other molecular and ionic species found in nature. The term "herbal" and variants thereof, as used herein, refers to edible vegetable or plant substances or materials.

The methods of the present invention used for standardization of a biologically or pharmacologically active mixture of chemical components obtained from a biological source, preferably a plant involve initially conducting a plurality of different processes using a plurality of samples from the same biological source, preferably plant source, to produce a plurality of products. The isolated products are then subjected to pharmacological tests and the product demonstrating the highest pharmacological activity in the test is selected. The specific process used to produce the selected product is then repeated to produce a test product. Physical and/or chemical tests are then performed on both the selected product and the test product to provide qualitative and, in most instances, quantitative information regarding the chemical component(s) of the products. The pharmacological tests initially employed with the plurality of products are then repeated on the test product. The qualitative and quantitative information, or "chemical fingerprints" as they are sometimes referred to, and the pharmacological activity of the selected product and the test product are compared with one another. In those situations in which the chemical component or component(s) of the test product are present in an amount which differs no more than about plus or minus 10% from the amount of the same chemical component(s) of the selected product and the pharmacological activity of the test product differs no more than about plus or minus 10% percent from the corresponding pharmacological activity of the selected product, then the process used to produce the selected product is chosen as the standard process for producing the pharmacologically active mixture. In addition, assuming that the highest pharmacological activity is being sought, that mixture having the highest pharmacological activity as determined by the pharmacological test (or "pharmacological fingerprint") and identified by the physical and/or chemical test (or "chemical fingerprint") may also be selected as the preferred pharmacologically active mixture.

Generally the processes being considered are similar or generically the same. For example, when the source of the mixture of the chemical components is a plant source, such as a mixture used in an herbal medication or composition, typical processes may include methods of harvesting, methods of storage, methods of expressing liquid components and, preferably, methods of extraction of chemical components, most preferably the chemical components responsible for pharmacological activity. A method is chosen for a particular process and variables are changed, when possible, one at a time to produce a plurality of method products. In a method of extraction, the preferred selected product and test product would be a selected plant extract (obtained from a plurality of plant extracts) and test plant extract, respectively.

The pharmacological tests performed on the process products, preferably plant extracts, may be in the form of in vitro and/or in vivo pharmacological tests. In the present invention it is preferred that at least two in vitro and at least two in vivo pharmacological tests be used. These tests are generally correlated with a changed biological state of a living organism. This may take the form of either an enhanced condition of the organism or an effective treatment of a medical condition in a patient. Examples of the enhanced condition may be as a stimulant, such as to produce a heightened wakened state, a sedative effect, etc.

The product, preferably a plant extract when an herbal material is under consideration, is selected which displays the best or highest pharmacological activity. This corresponds to the most pronounced enhancement of biological state or that which produces the most desirable medical condition in a patient.

In obtaining the test product, such as a test extract when an extraction process is being tested, the identical conditions used to obtain the selected product, such as the selected plant extract are duplicated.

BRIEF DESCRIPTION OF THE DRAWINGS

FIG. 26 shows that NGF increased neurite outgrowth in PC12 in a dose-dependent manner seven days after treatment.

FIG. 27 shows that HT-1001 increased neurite outgrowth in PC12 in a dose-dependent manner seven days after treatment.

FIG. 28 shows that HT-1001 increased neurite outgrowth in N1E-115 in a dose-dependent manner seven days after treatment.

FIG. 29 shows control cells.

FIG. 30 shows cells treated with CVT-E001.

MODE(S) FOR CARRYING OUT THE INVENTION

Figure 1:
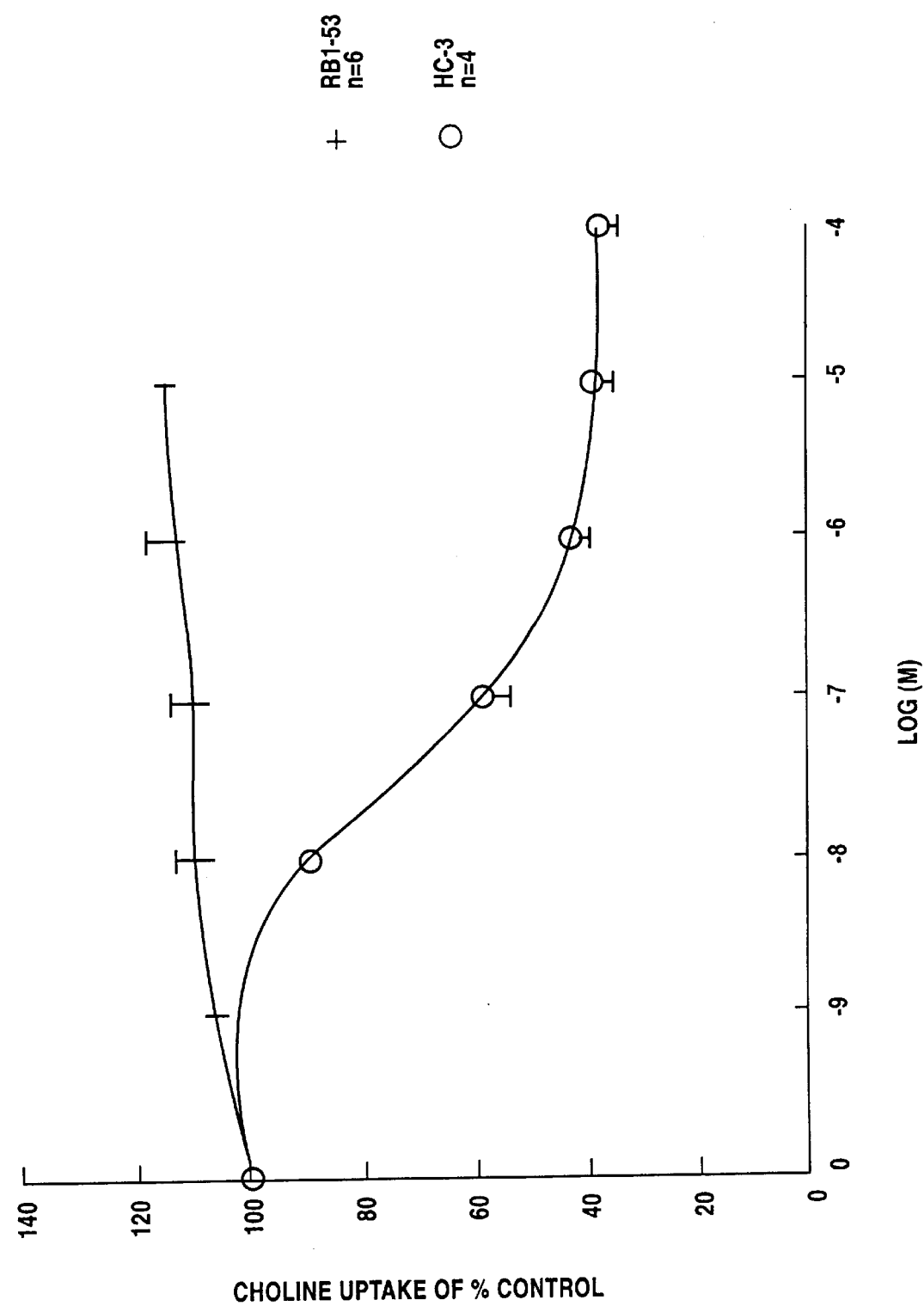
FIG. 1 shows the effects of various doses of $Rb_1$ and HC3 on choline uptake by rat brain synaptosomes.

The methods of the present invention are expected to have most widespread application in differentiating, improving and achieving reproducibility or standardization of herbal processing techniques, particularly extraction of pharmacologically active mixtures from plant sources and in obtaining plant extracts of high pharmacological activity. The reproducibility and standardization procedures of the invention involve the use of a combination of pharmacological and chemical fingerprinting of the isolated products, typically obtained in extraction procedures.

Chemical Fingerprinting:

Chemical fingerprinting is a process whereby a single compound or a mixture of compounds, for example an herbal pharmaceutical mixture, is tested to obtain a qualitative, and in many instances quantitative, information which is characteristic of the chemical compound(s) present. The presence of these characteristic components in appreciable and characteristic quantities provides chemical uniqueness which may be related to the pharmacological properties of the component(s). Preparatory to or integral in chemical fingerprinting is subjecting a sample, frequently an extract when fingerprinting is applied to a material obtained from a plant source, to a separation procedure involving chromatographic or electrophoretic methods and subsequent analysis of the chemical components eluted in the separation method. A number of detection methods may be employed in forming the actual chemical fingerprint of the eluted chemical components. The most appropriate method of separation of the chemical components obtained from an herbal pharmaceutical composition is high performance liquid chromatography (HPLC) and characterization of the eluted chemicals is by ultraviolet absorbance detection and electrospray mass spectrometry in series. This method of analysis provides the most unequivocal characterization of a complex mixture of chemical components, such as those found in herbal pharmaceutical preparations. Data obtained from such fingerprinting provides not only information concerning the chemical characteristics of the chemical components of the herbal pharmaceutical preparation but also information regarding its authenticity, purity, and consistency of composition of samples provided.

Chemical fingerprinting of a complex chemical mixture, such as an herbal pharmaceutical product, involves solubilization of the components of the chemical mixture, frequently involving making a soluble extract of an herbal pharmaceutical product. The solution or extract is then subjected to a separatory procedure which separates the mixture into groups of components or, preferably, individual components. Such a separatory procedure, when combined with a chemical analysis method, permits the identification, frequently unequivocal, of important chemical constituents which are normally found in, and are characteristic of the product.

The separatory procedure employed is preferably a chromatographic procedure such as high performance liquid chromatography (HPLC), electrophoresis (gel or capillary), thin layer chromatography (TLC) and gas chromatography (GC). In order to obtain samples which can be subsequently pharmacologically evaluated, HPLC is the preferred method. Preferable detection systems in the case of HPLC, include absorbance and fluorometric spectroscopy, refractive index, electrochemical methods, evaporative light scattering, electrospray mass spectrometry, or a combination of these. In the case of GC, electron capture, sodium-phosphorus or mass spectrometric detectors are often used. When TLC and electrophoretic separation methods are employed, various calorimetric and/or mass spectrometric detection methods are employed. In the case of herbal pharmaceutical products, the use of HPLC with a combination of ultraviolet absorbance detection and electrospray mass spectrometry provides an absorbance fingerprint and assigns a molecular mass to many of the absorbing components. The combination of elution profile from the column, absorbance characteristics and molecular mass characteristics provides an identification, both qualitative and quantitative, of the individual chemical constituents of the herbal product.

Chemical fingerprinting is generally performed using HPLC combined with absorbance and electrospray mass spectrometric detection. The following description deals with the fingerprinting of CVT-E001.

Briefly, the herbal product of interest is extracted in an appropriate solvent, often water, alcohol, acetonitrile, ethyl acetate or combinations of these solvents (tinctures can often be analyzed without further processing). The extract is then filtered to remove any particulates and dried to remove interfering solvents. The extract may be stored frozen until analysis. When analysis is to be performed the extract is dissolved in an appropriate solvent. Typically 20% acetonitrile containing 0.05% trifluoroacetic acid (TFA) can be used, however this can be altered depending on the solubility of the extract to be analyzed. A known amount of the extract is then applied to the HPLC apparatus (typically the equivalent of 1 mg or less in 100 ml solvent is analyzed). The HPLC apparatus can be any one of a number of available models which possess flow rate ranges of 0.01 ml to 5 ml per minute or greater and have a capacity to provide a solvent gradient although isocratic systems can also be used. Typically the separation of the chemical constituents of the herbal product can be achieved using a gradient elution of water, acetonitrile and TFA. Solvent A consists of water or water containing a low amount of acetonitrile (2%–5%) and 0.05% TFA. Solvent B consists of a high concentration of acetonitrile (70%–95%) with 0.05% TFA. The flow rate is usually 1 ml per minute (0.5 ml–1.5 ml per minute or other flow rates can be used). A gradient running from low amounts of solvent A to high amounts of solvent B is used. This gradient can be varied in order to isolate selected chemical components. An example gradient could involve the following: Solvent A (5% acetonitrile, 0.05% TFA), Solvent B (70% acetonitrile, 0.05% TFA); flow rate 1 ml/min.; At time=0 minutes the mobile phase consists of 100% solvent A. At time=30 minutes the mobile phase consists of 100% solvent B. Between 0 and 30 minutes the gradient change is linear. Between 30 and 35 minutes the mobile phase consists of 100% solvent B. Between 35 and 40 minutes the solvent is returned to 100% solvent A and the separation system reequilibrated prior to the analysis of a subsequent sample.

While HPLC is the preferred test for chemical fingerprinting, it is possible to use TLC, protein determination, carbohydrate determinations, organic extractions or other methods of chemical analysis, as will be clear to those in the art.

Separation is achieved on an analytical high performance liquid chromatographic column (usually 4.6 mm internal diameter by 25 cm in length) although other sizes may be used (e.g. 1 mm by 25 cm). The column may contain any one of a number of packing materials used to separate chemicals (reverse phase materials, silica, hydrophilic interaction materials etc.). Typically a reverse phase column containing $C_8$ reverse phase material is used.

Detection of the chemicals of interest involves the use of the applicable detectors mentioned previously. Typically a combination of ultraviolet absorbance and electrospray mass spectrometry is used. Immediately after elution from the HPLC column the solvents containing the compounds of interest pass through an ultraviolet absorbance detector and the absorbance is recorded, thereby providing a typical absorbance profile (a number of wavelengths can be monitored depending on the absorbance characteristics of the chemicals of interest). Immediately following passage through the ultraviolet absorbance detector the solvent containing the chemicals of interest continues into an electrospray mass spectrometric detector. In the case of analytical columns a certain amount of the flowing solvent is split off as the electrospray apparatus can only accommodate small flows of solvent (50–100 ml/min. at most). In the case of smaller columns all of the mobile phase may be permitted to enter the electrospray apparatus. In the case of analytical columns the split typically permits 10% or less of the flow to enter the electrospray apparatus while the remaining 90% or more of the flow can be collected as fractions containing specific chemicals for later pharmacological evaluation. Chemicals which enter the electrospray mass spectrometer will provide positively charged ions for positive mode analysis if they take a proton (certain amines, steroids or flavones for example). Such chemicals will be able to provide information as to their exact chemical mass and may provide further chemical identification by means of their fragmentation patterns. Chemicals which do not take a charge but rather lose a proton in basic circumstances (sugars, some phenols and carboxylic acids) must be examined in a slightly different manner. In the case of chemicals which do not take a charge individual fractions are collected following elution from the column and passage through the appropriate detector (ultraviolet absorbance or refractive index detectors for example). Each fraction is then dried and then reconstituted in an appropriate solvent (50% acetonitrile in water mixed with 10% ammonium hydroxide for example) and injected directly into the electrospray apparatus which is operating in negative mode. Again, information as to the exact chemical mass and further chemical identification by means of their fragmentation patterns is provided.

Thus the combination of elution pattern, ultraviolet absorbance characteristics and chemical mass and fragmentation patterns provide extensive information regarding the identification of individual characteristic chemicals found in the herbal product. This information tells the researcher whether the samples are authentic with characteristic chemical features and, when compared to standards containing known amounts of the selected chemicals, can provide a quantitative estimate of the amounts of selected chemicals present. Information as to possible adulterants can be provided if extraneous chemicals appear in the analysis. The information provided will inform the researcher whether the material contains the desired substances and in what quantity (i.e. quality control) and, possibly, whether adulterants are present. This would allow for informed purchases of raw materials and provide evidence for consistency in quality of materials being produced and sold to the consumer.

Example of Application of Chemical Fingerprinting to a Herbal Extract

CVT-E001 is a specific extract of American ginseng (*Panax quinquefolium L.*). It is known to be rich in a number of characteristic saponins and fatty acids. Table 1 lists a number of saponins characteristic of *Panax quinquefolium* and other *Panax* species. CVT-E001 is claimed to have properties including the ability to stimulate choline uptake and enhance learning and memory in animal models. Two lots of CVT-E001 were examined and a chemical fingerprint generated using high performance liquid chromatography (HPLC) coupled to ultraviolet absorbance detection and electrospray Table 1. Saponins characteristic of *Panax quinquefolium* and other *Panax* species.

| Saponin | Chemical Formula | Molecular Weight |
|---|---|---|
| Rb1 | $C_{54}H_{92}O_{23}$ | 1109.3 |
| Rc | $C_{53}H_{90}O_{22}$ | 1079.3 |
| Rg1 | $C_{42}H_{72}O_{14}$ | 801.0 |
| Re | $C_{48}H_{82}O_{18}$ | 947.2 |
| Rd | $C_{48}H_{82}O_{18}$ | 947.2 |
| Quinquenoside R1 | $C_{56}H_{94}O_{24}$ | 1151.3 |

10 mg each of lot 3 and 4 of the CVT-E001 product were dissolved in separate vials in 1.0 ml of 5% acetonitrile in water with 0.05% trifluoroacetic acid (TFA).

100 ml of these stocks representing 1 mg of original material were individually applied to the HPLC apparatus. The chromatographic system consisted of a Hewlett Packard 1050 gradient HPLC system equipped with an autoinjector and ultraviolet absorbance detector. The column consisted of a Zorbax 300SB-C8 reverse phase column (4.6 mm×25 cm).

The separation was achieved using a gradient elution consisting of water, acetonitrile and TFA. Mobile phase A was 5% acetonitrile in water with 0.05% trifluoroacetic acid as counter ion. Mobile phase B was 70% acetonitrile in water with 0.05% trifluoroacetic acid as counter ion. Flow rate was 1.0 ml/minute. At time=0 minutes the mobile phase consisted of 100% A. At 30 minutes the mobile phase was 100% B and between 0 and 30 minutes the gradient change was linear. Between 30 and 35 minutes the mobile phase was 100% B. Between 35 minutes and 40 minutes the mobile phase returned to 100% A from 100% B. A minimum 10 minute wash period in 100% A was performed prior to another injection. Ultraviolet absorbance was monitored at 203 nm.

Electrospray mass spectroscopy was performed using a Fisons Instruments VG Quatro instrument. Following elution from the ultraviolet absorbance detector the flow from the HPLC equipment was split and 2% (20 ml/minute) was fed into the electrospray instrument. Chemicals eluting from the HPLC instrument were monitored in positive mode for mass between 200 and 1200 molecular weight. A number of chemicals provided mass spectra characteristic of this product.

Figure 25:
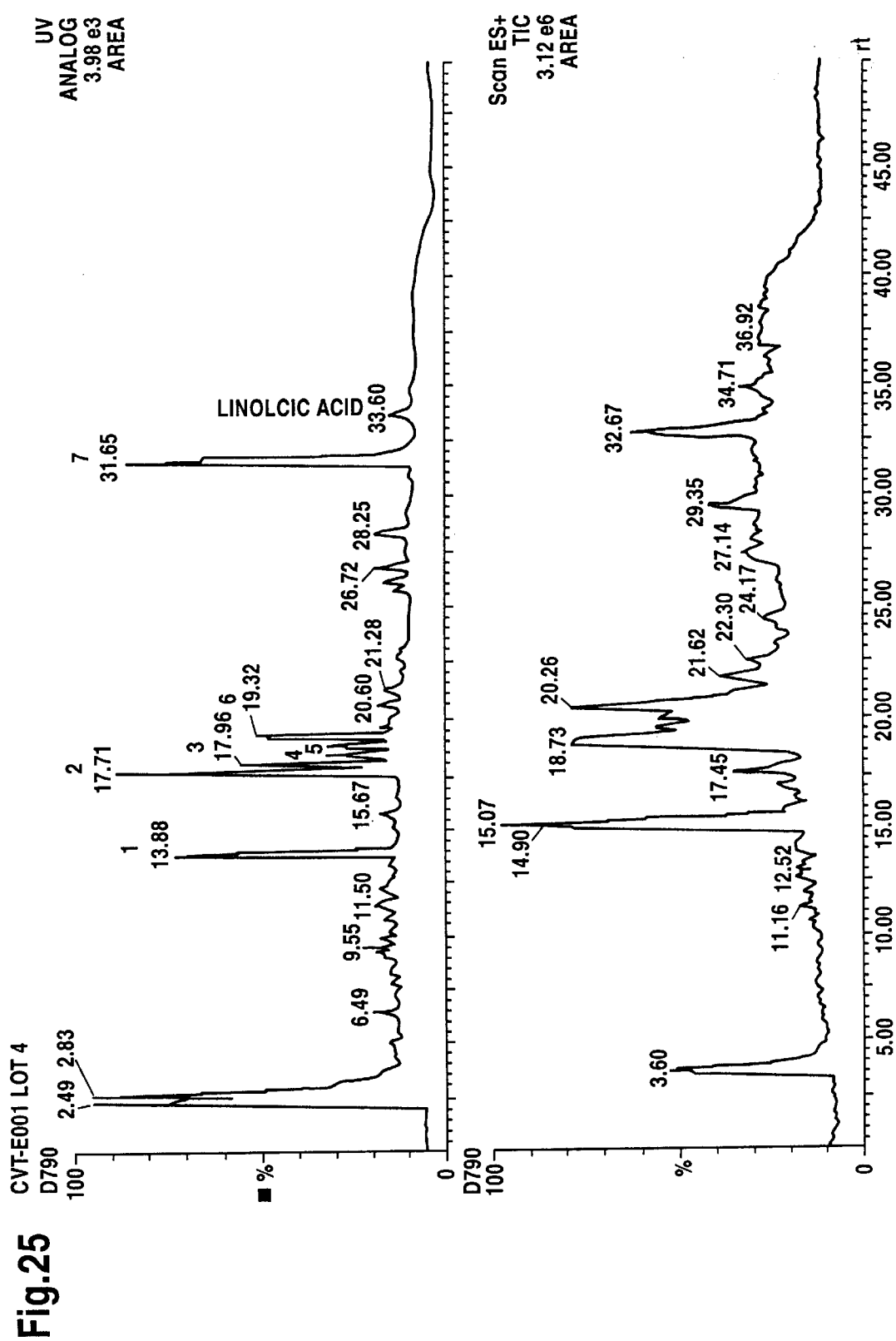
FIG. 25 provides ultraviolet absorbance characteristics (uv ANALOG) and total ion counts (TIC) for lot 4 of CVT-E001.

FIGS. 25 and 25 provides ultraviolet absorbance characteristics (uv ANOLOG) and total ion counts (TIC) for lots 3 and 4 respectively.

Both lots provide almost identical ultraviolet absorbance chromatograms with the salient features being a distinct peak at 13.7–13.9 minutes, 5 distinct peaks between 17.6 and 19.4 minutes a distinct peak at 31.7 minutes and another distinct peak at 33.6 minutes. Numerous lesser peaks are also distinctive. The seven most prevalent peaks have been designated 1 through 7.

Figure 2:
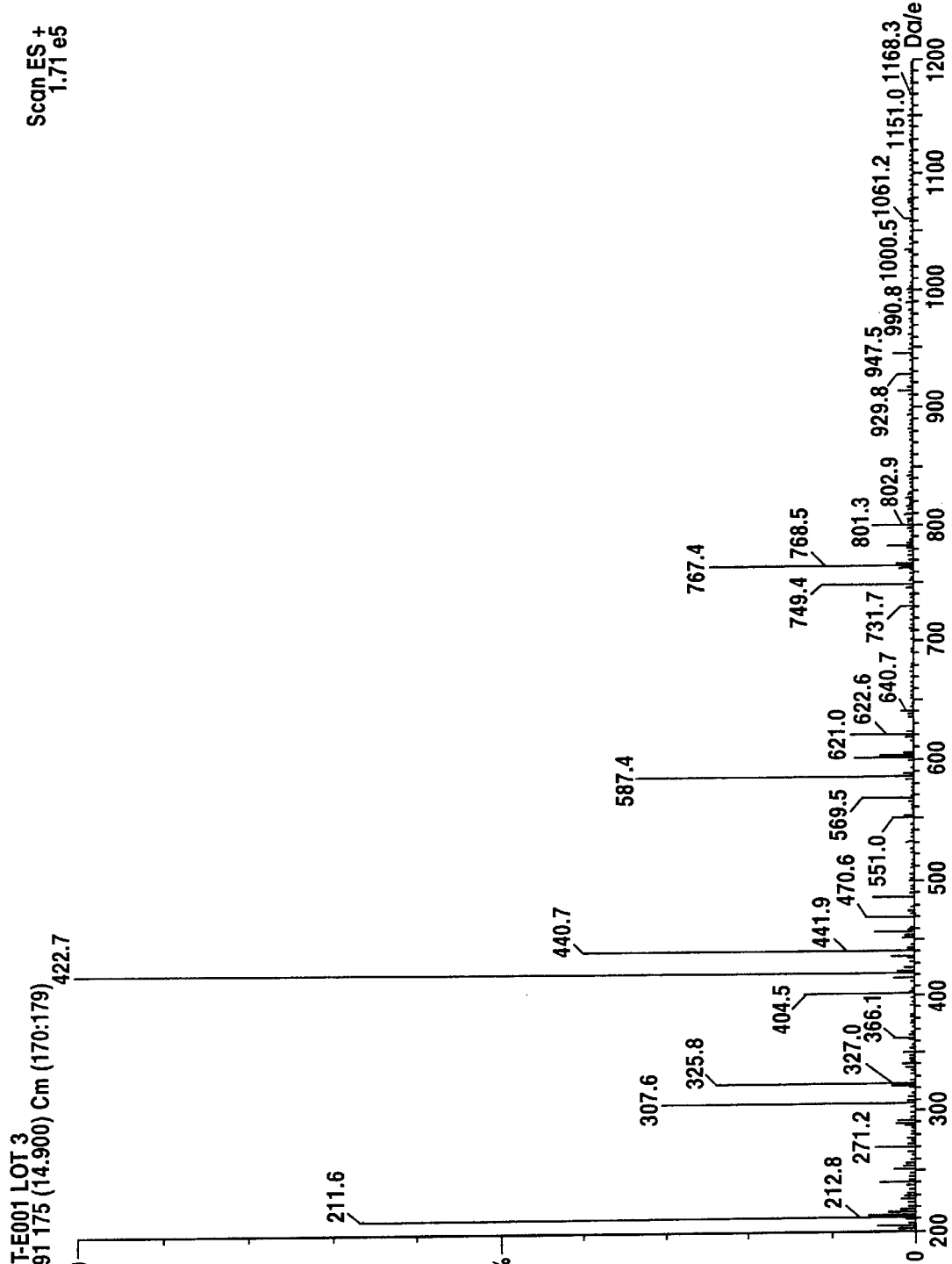
FIG. 2 shows an electrospray mass spectrum obtained from a mixture of ginsenoside $Rg_1$ and ginsenoside Re co-eluting from a sample of CVT-E001 Lot 3 (see FIG. 24 for corresponding chromatographic trace). Due to isotope effects these large molecules have an inherent error in mass measurements. Signals are reported with an error of about one mass unit. For $Rg_1$ the protonated mass (M+H) is 801 and for Re the protonated mass (M+H) is 948.
Figure 3:
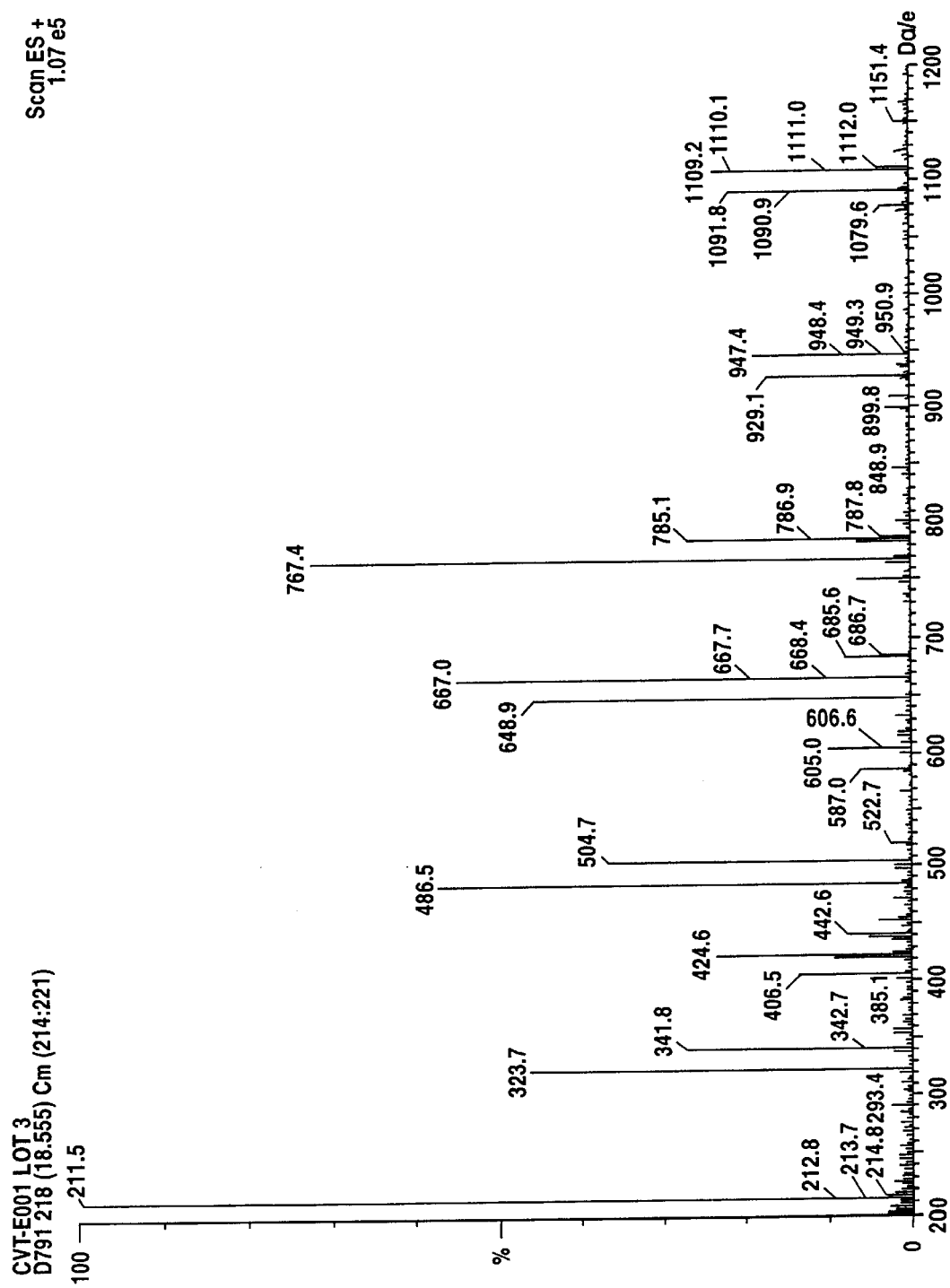
FIG. 3 shows an electrospray mass spectrum obtained from ginsenoside $Rb_1$ eluting from a sample of CVT-E001 Lot 3 (see FIG. 24 for corresponding chromatographic trace). Due to isotope effects these large molecules have an inherent error in mass measurements. Signals are reported with an error of about one mass unit. Protonated mass (M+H) is 1110.
Figure 4:
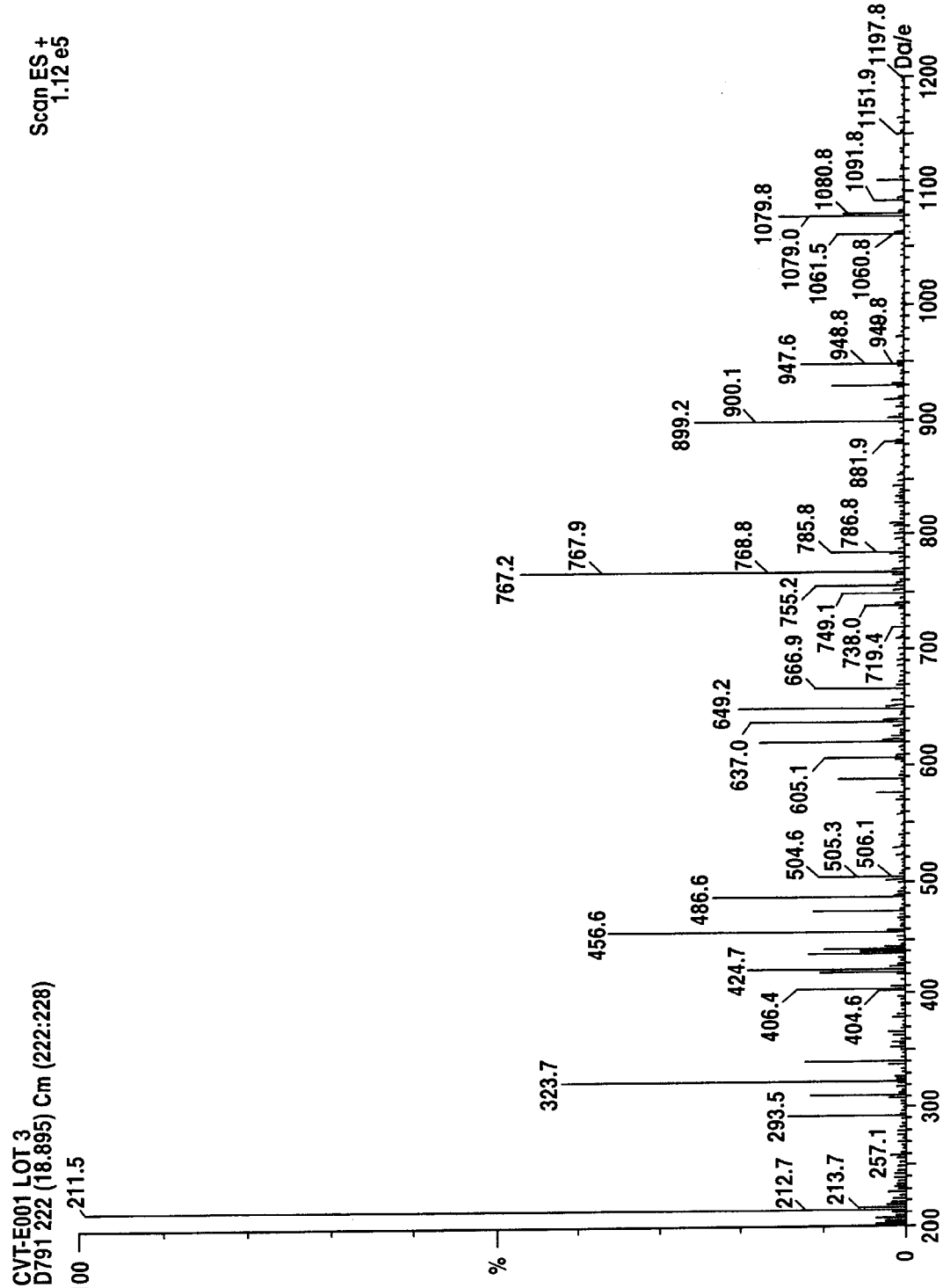
FIG. 4 shows an electrospray mass spectrum obtained from ginsenoside Re eluting from a sample of CVT-E001 Lot 3 (see FIG. 24 for corresponding chromatographic trace). Due to isotope effects these large molecules have an inherent error in mass measurements. Signals are reported with an error of about one mass unit. Protonated mass (M+H) is 1080.
Figure 5:
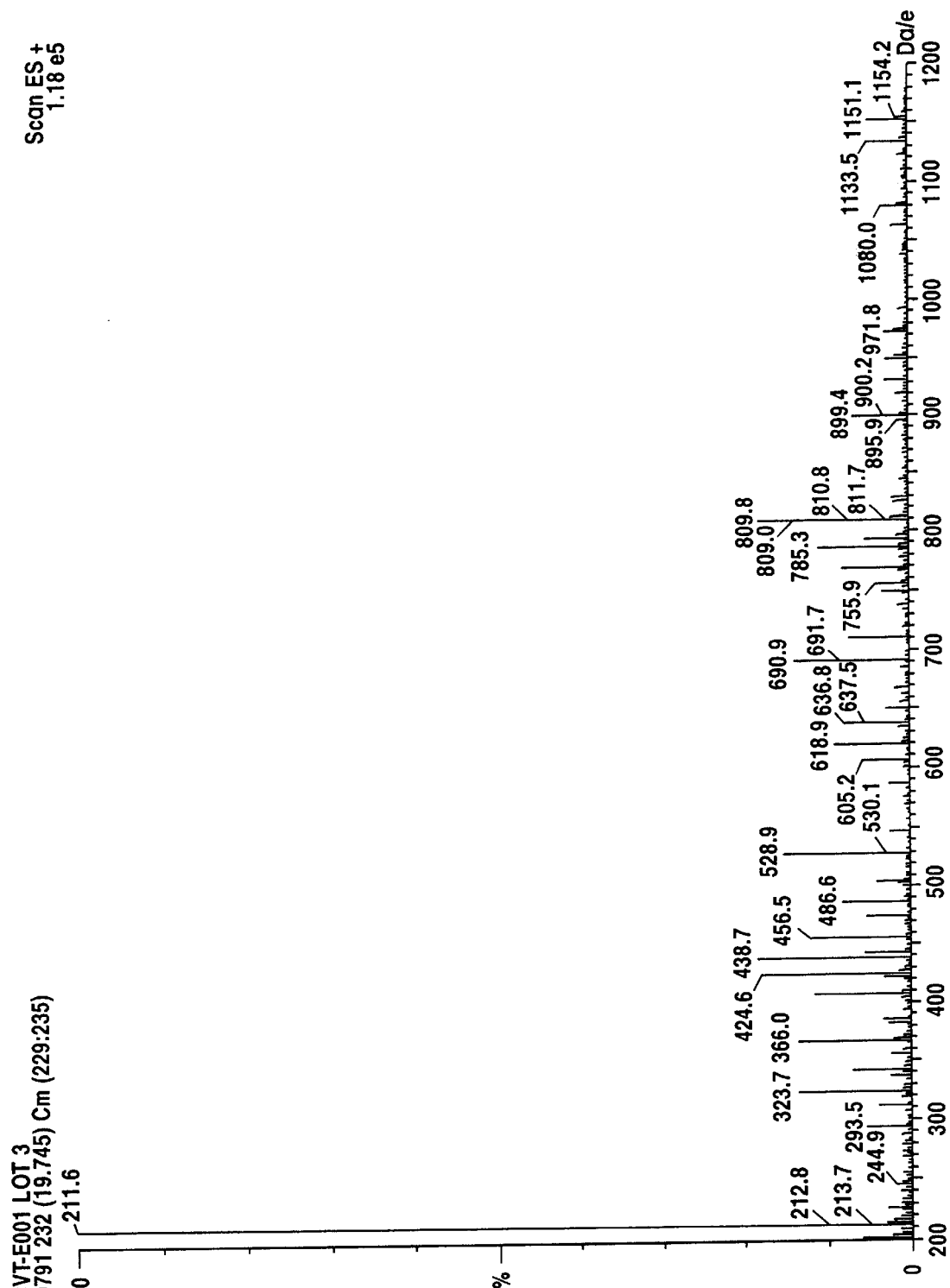
FIG. 5 shows an electrospray mass spectrum obtained from quinquenoside $R_1$ eluting from a sample of CVT-E001 Lot 3 (see FIG. 24 for corresponding chromatographic trace). Due to isotope effects these large molecules have an inherent error in mass measurements. Signals are reported with an error of about one mass unit. Protonated mass (M+H) is 1151.
Figure 6:
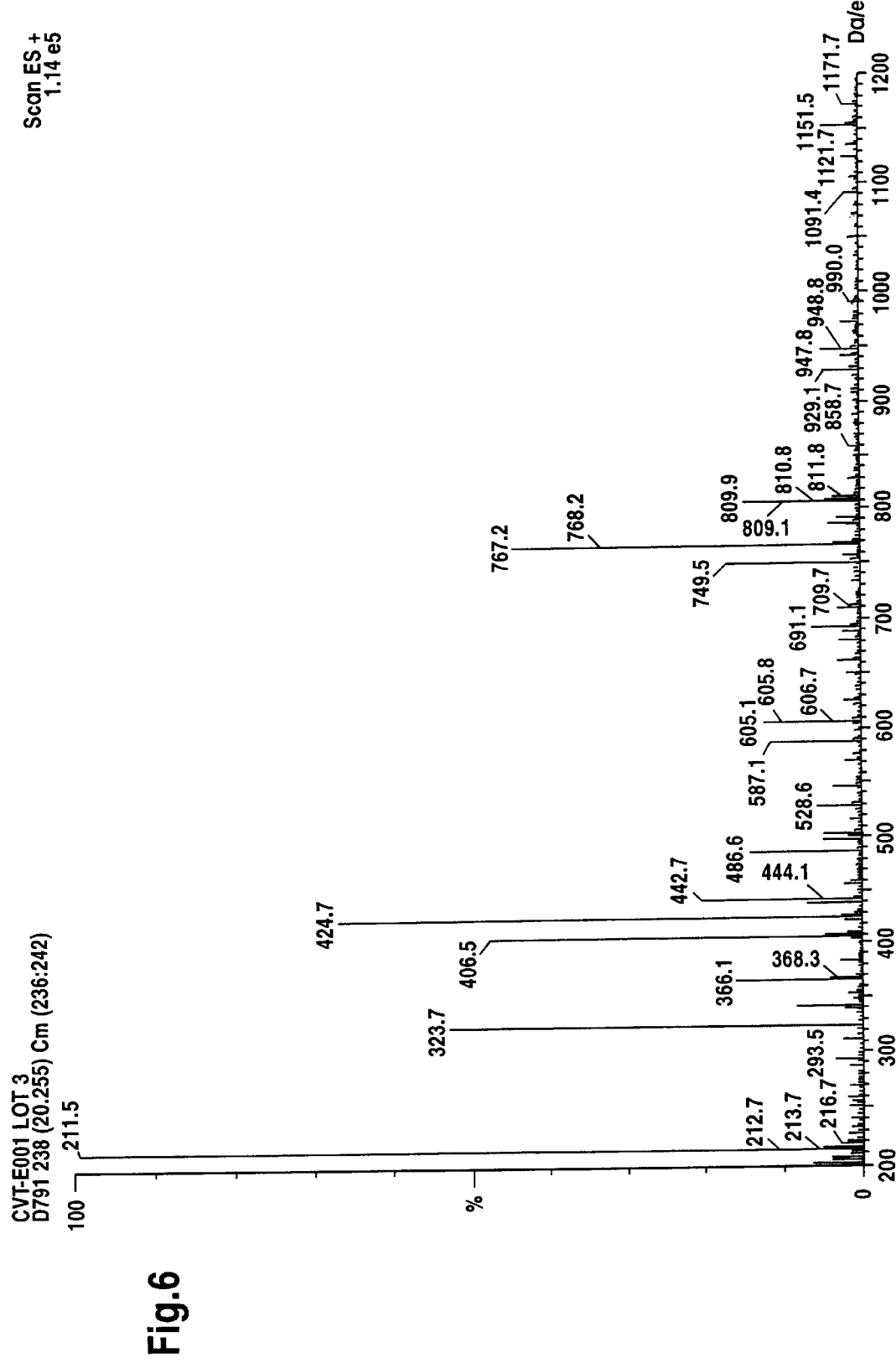
FIG. 6 shows an electrospray mass spectrum obtained from ginsenoside Rd eluting from a sample of CVT-E001 Lot 3 (see FIG. 24 for corresponding chromatographic trace). Due to isotope effects these large molecules have an inherent error in mass measurements. Signals are reported with an error of about one mass unit. Protonated mass (M+H) is 948.
Figure 7:
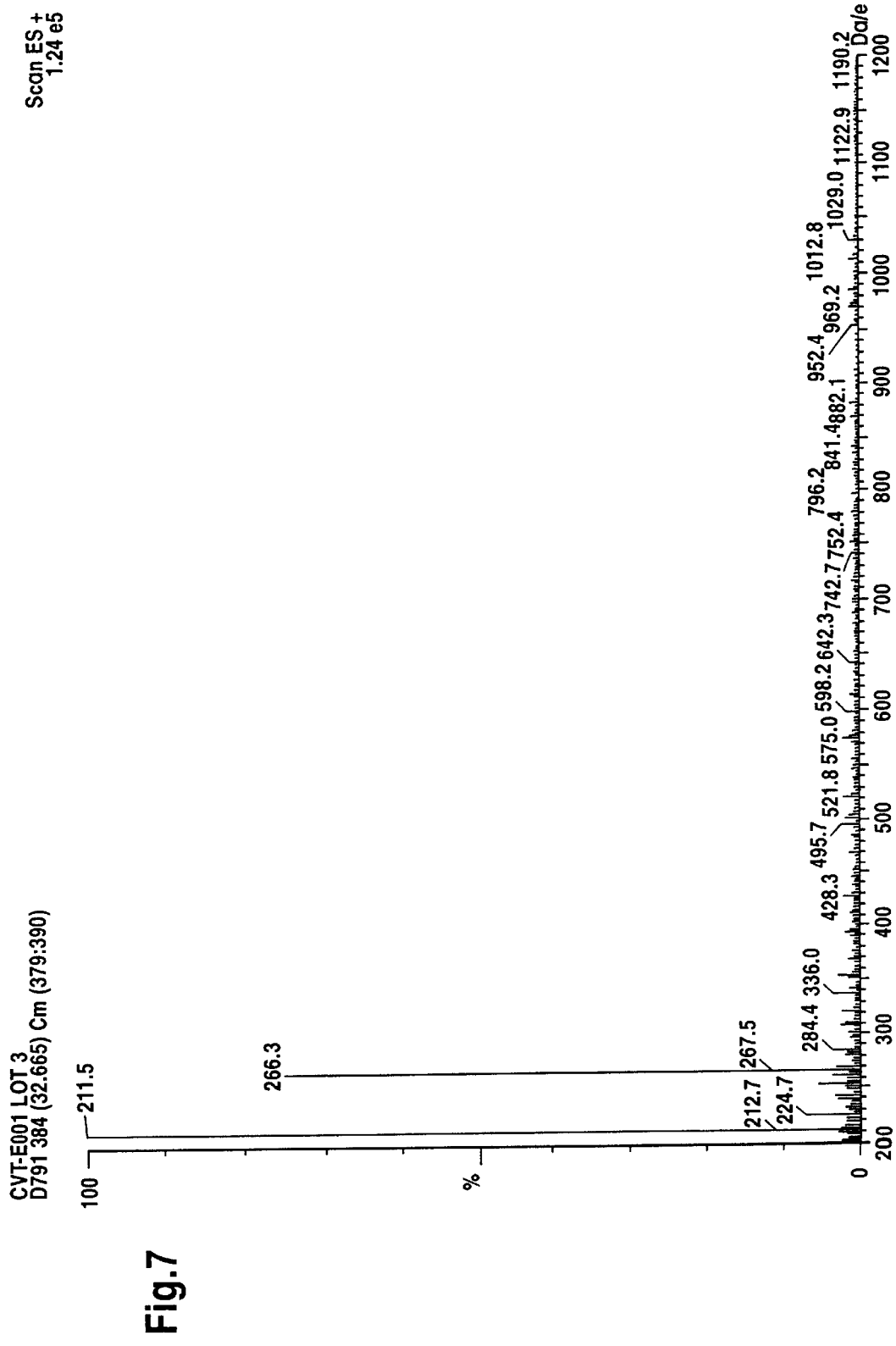
FIG. 7 shows an electrospray mass spectrum obtained from a characteristic unidentified compound eluting from a sample of CVT-E001 Lot 3 (see FIG. 24 for corresponding chromatographic trace). Signals are reported with an error of about one to two mass units. Protonated mass signal (M+H) is 266.
Figure 8:
FIG. 8 shows an electrospray mass spectrum obtained from a mixture of ginsenoside $Rg_1$ and ginsenoside Re co-eluting from a sample of CVT-E001 Lot 4 (see FIG. 25 for corresponding chromatographic trace). Due to isotope effects these large molecules have an inherent error in mass measurements. Signals are reported with an error of about one mass unit. For $Rg_1$ the protonated mass (M+H) is 801 and for Re the protonated mass (M+H) is 948.
Figure 9:
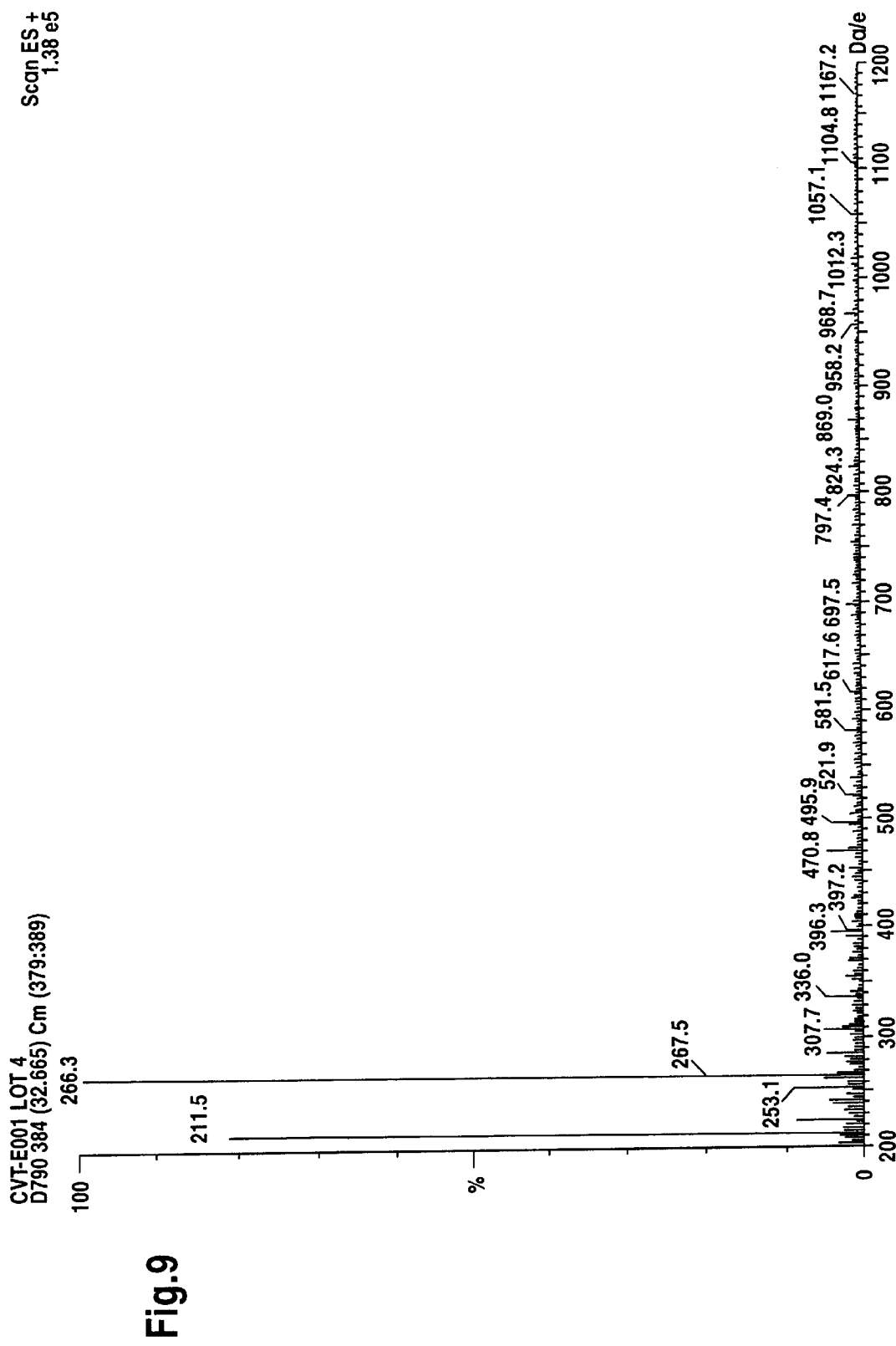
FIG. 9 shows an electrospray mass spectrum obtained from a characteristic unidentified compound eluting from a sample of CVT-E001 Lot 4 (see FIG. 25 for corresponding chromatographic trace). Signals are reported with an error of about one to two mass units. Protonated mass signal (M+H) is 266.
Figure 10:
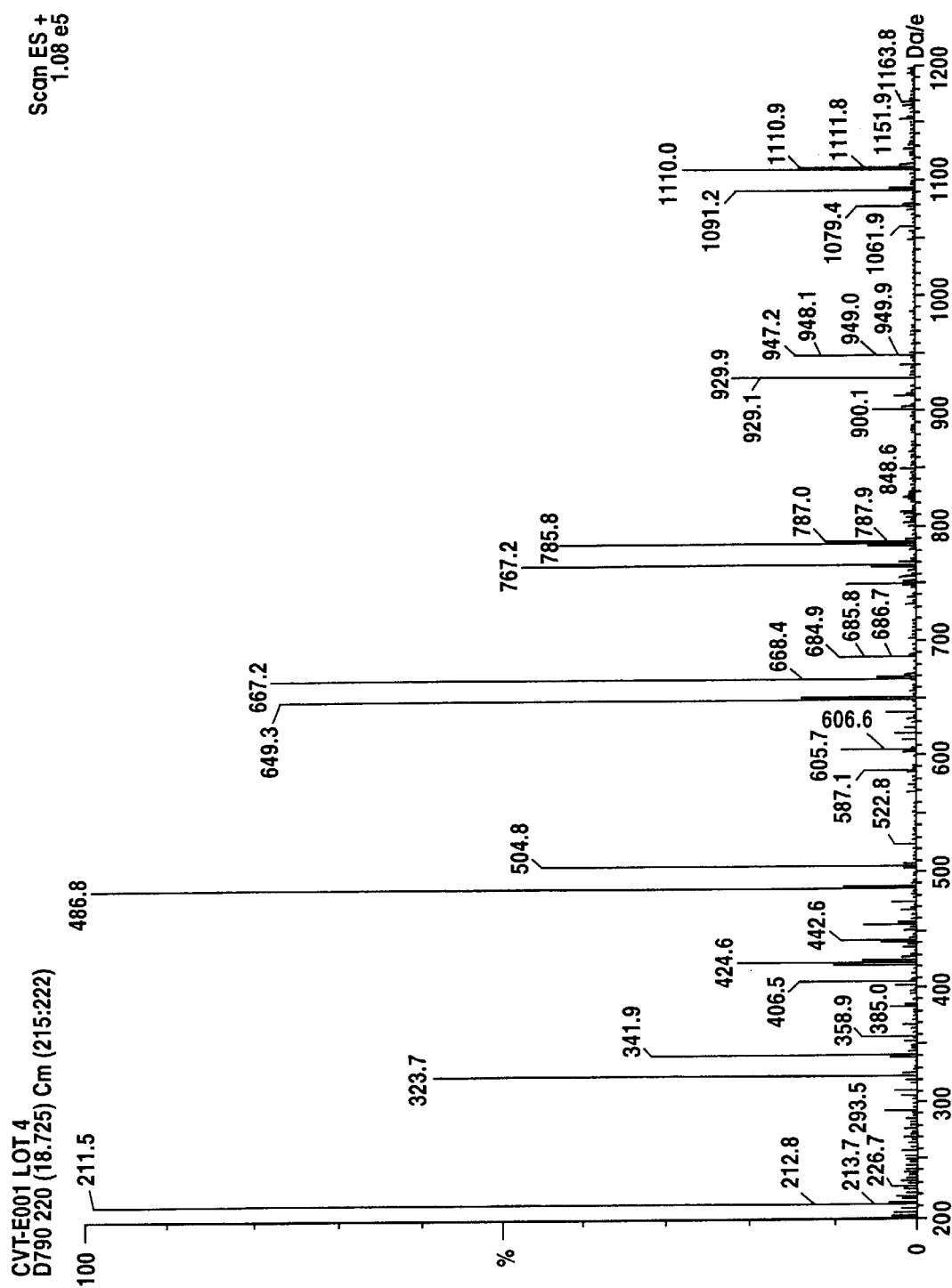
FIG. 10 shows an electrospray mass spectrum obtained from ginsenoside $Rb_1$ eluting from a sample of CVT-E001 Lot 4 (see FIG. 25 for corresponding chromatographic trace). Due to isotope effect these large molecules have an inherent error in mass measurements. Signals are reported with an error of about one mass unit. Protonated mass (M+H) is 1110.
Figure 11:
FIG. 11 shows an electrospray mass spectrum obtained from ginsenoside Re eluting from a sample of CVT-E001 Lot 4 (see FIG. 25 for corresponding chromatographic trace). Due to isotope effects these large molecules have an inherent error in mass measurements. Signals are reported with an error of about one mass unit. Protonated mass (M+H) is 1080.
Figure 12:
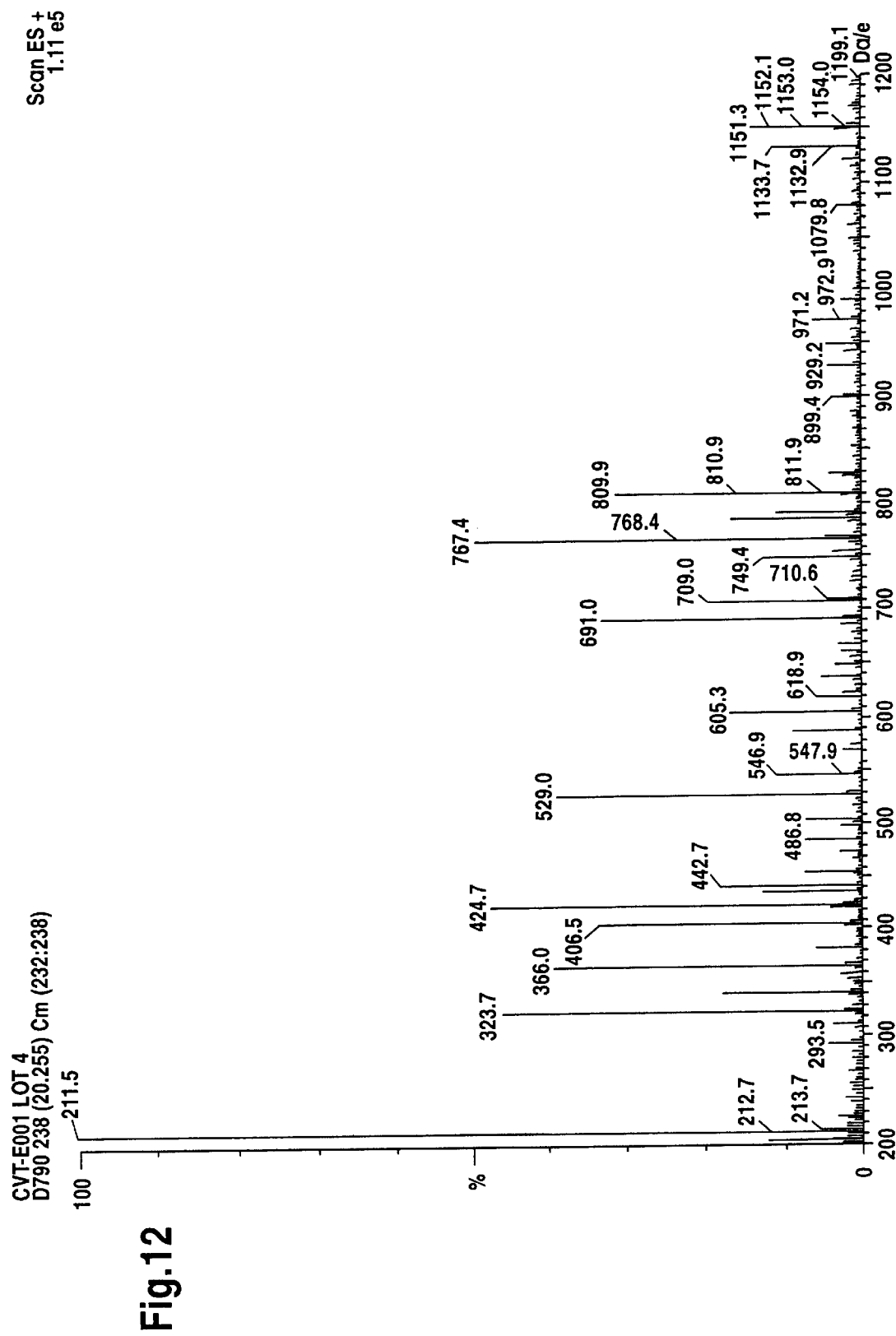
FIG. 12 shows an electrospray mass spectrum obtained from Quinquenoside $R_1$ eluting from a sample of CVT-E001 Lot 4 (see FIG. 25 for corresponding chromatographic trace). Due to isotope effects these large molecules have an inherent error in mass measurements. Signals are reported with an error of about one mass unit. Protonated mass (M+H) is 1151.
Figure 13:
FIG. 13 shows an electrospray mass spectrum obtained from pure ginsenoside $Rb_1$. Due to isotope effects this large molecule has an inherent error in mass measurements. Signals are reported with an error of about one mass unit. Protonated mass (M+H) is 1110.

As the mobile phase flows from one detection instrument to the other there is an approximate 1 minute delay between recording the ultraviolet signal and the mass spectra signal. As a result the total ion count event at 14.90 minutes corresponds to the ultraviolet absorbance event at 13.71 minutes. The following figures (FIGS. 3–13) illustrate the mass spectra obtained for a number of ion count events and are characteristic of chemicals found in CVT-E001. Each ion event is identified by numbers in the upper left corner of the spectrum. For example as it appears in FIG. 2, D791 175 (14.900) CM (170:179) refers to chromatogram run number D791, where the spectrum is centered on scan number 175 at 14.900 minutes and is derived from a combination of scans 170 to 179.

The following is a list of masses associated with each of the seven prominent peaks and where possible identification of those peaks. M+H refers to the molecular mass plus one proton.

Peak 1 M+H 801, Fragments 423, 440, 587, 767. Identified as ginsenoside Rg1 MW=800. Also present in ginsenoside Re M+H 948 MW=947. These compounds cochromatograph and provide a combined spectra.

Peak 2 M+H 1110, Fragments 767, 486, 667, 947. Identified as ginsenoside Rb1 MW=1109

Peak 3 M+H 1180, Fragments 899, 456, 637. Identified as ginsenoside Rc MW=1079

Peak 4 Mass unresolved as signal is overshadowed by other components.

Peak 5 Mass unresolved as signal is overshadowed by other components.

Peak 6 M+H 1151, Fragments 767, 424, 529, 323. Identified as quinquenoside R1. This is an acetylated form of Rb1 which is found in *Panax quinquefolium* and has not been reported in other *Panax* species. The structure is illustrated below.

Chemical structure of quinquenoside R1 which is characteristic of *Panax quinquefolium* extracts.

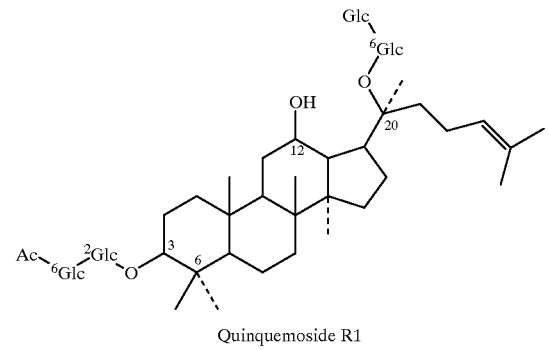

Quinquemoside R1

Peak 7 M+H 266. Identity unknown.

The small peak at 33.6 minutes has been identified as linoleic acid.

Figure 14:
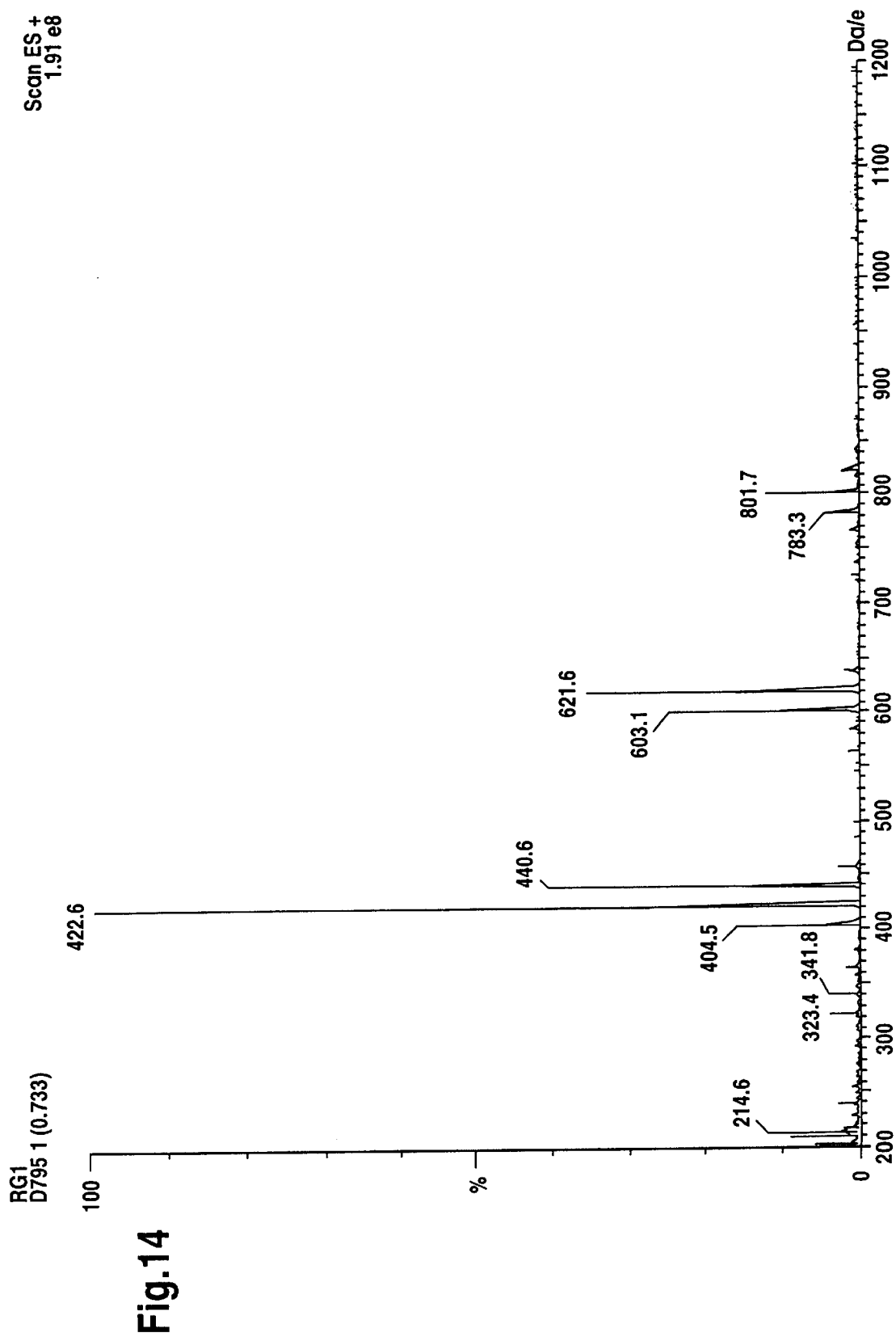
FIG. 14 shows an electrospray mass spectrum obtained from pure ginsenoside $Rg_g$. Due to isotope effects this large molecule has an inherent error in mass measurements. Signals are reported with an error of about one mass unit. Protonated mass (M+H) is 802.

Spectra of pure ginsenosides Rb1 and Rg1 are also provided for comparison to those obtained from CVT-E001 samples (FIGS. 14 and 15) respectively.

Lots 3 and 4 of CVT-E001 each produce a characteristic ultraviolet absorbance chromatogram when separated in the manner described. Electrospray mass spectrometry provides unequivocal identification of a number of the chemicals separated by the HPLC method and characteristic of CVT-E001. The two samples are definitely derived from *Panax quinquefolium* and are chemically comparable.

Pharmacological Fingerprinting

Pharmacological fingerprinting involves testing a sample of a chemical compound or compounds to determine whether there is pharmacological activity inherent in the material. The pharmacological properties or pharmacological activity of the sample depends on the particular biological or pharmacological model employed. Such models should appropriately test the biological enhancement of a biological state of an individual or effective treatment of a medical condition in a patient. Such patient is preferably a human but may be another animal such as a dog, cat, horse, etc. Accordingly, such pharmacological testing or fingerprinting involves in vivo and/or in vitro biological models. Typically the sample being tested exists as a pure compound(s) in a suitable pharmacological carrier, and/or solvent. In a preferred embodiment of the present invention, the sample is an herbal extract or a chromatographic fraction of an herbal extract.

Preferred pharmacological fingerprinting as used in the present invention involves taking both the original extract and the selected chromatographic fractions obtained from chromatographic procedures described in chemical fingerprinting which contain an isolated chemical(s) of interest and subjecting the chemical(s) found in these fractions to standardized pharmacological evaluations. While many different pharmacological evaluations can be conducted, in general the evaluations are limited to those indicative of processes supporting the intended effect of the chemical component(s) or herbal material being evaluated. In the present invention, it is most preferred that at least two in vivo and two in vitro biological models are evaluated to determine the biological activity of a sample or extract. It is also preferred that in each in vitro experiment, at least three doses of the extract and one solvent control group be included. It is also preferred in at least two models, the sample solution or extract should demonstrate significantly different pharmacological activity from the control group.

The biological or pharmacological models employed depend to a large extent on the components of the extract. For example, fractions of a ginseng extract containing oligosacchrides could be evaluated for their ability to stimulate the immune system. Two in vitro models might include total lymphocyites production and antibody production using mice or rat spleen. Two in vivo models might include serum total antibody and immunoglobumin G levels. Products for which claims of antidepressant activity have been made could be evaluated for monoamine oxidase A and B inhibiting ability in vitro and antidepressant activity in accepted behavioral tests such as the mouse forced swimming test and the locomotor activity test. An antihypertensive model may be evaluated by in vivo blood pressure determination in rats fed or injected intravenously with the extract under consideration and in vivo blood vessel and heart contractility assay, etc., whereas neuroprotectants may be evaluated by in vitro and in vivo enzymes and substrates involved in oxidative stress and neuroprotection assay, and antidepressants may be evaluated by their degree of monoamine oxidase inhibiting activity, increase of brain levels of noradrenaline and serotonin, decrease of brain levels of 5-hydroxyindoleactic acid, antidepressant-like and anxyiolytic-like effects in mouse forced swimming and black and white box test.

In some models, the activity of the extract is compared with one or more pure compounds derived from the extract. The result is analyzed to demonstrate a synergistic effect of the mixed compound in the extract. This provides the advantage of claiming the use of an extract over one single compound in terms of increased potency and possible decrease of side effects. Example of Application of Pharmacological Fingerprinting to an Herbal Extract, CVT-E001.

Chemical standardized herbal extract, CVT-E001 with a characteristic chemical fingerprinting described above is evaluated for its pharmacological properties in improving memory. The biological models were chosen based on the findings: (a) a deficit in cholinergical system in central nerve system is evident in Alzheimer's disease (AD). (b) an increase in monoamine oxidase B (MAO-B) activity has been reported in aging rats and in demented patients, etc. The following experiments in biological models were conducted and the results form the pharmacological fingerprinting of CVT-E001. The positive results shown in each experiment indicate CVT-E001 is useful as treatment for cognitive and memory impairment conditions such as Alzheimer's disease.

(1) Effects of CVT-E001 on choline uptake in isolated brain synaptosomes in rats Rationale Ginsenoside $Rb_1$ has been demonstrated to increase choline uptake (Benishin, 1992). A decrease in the production of the neurotransmitter acetylcholine is associated with memory loss and Alzheimer's disease. $Rb_1$ has been demonstrated to increase choline uptake into neurons and this presumably, enhances acetylcholine production which, in turn, alleviates memory impairment. In order to properly assert that CVT-E001 has properties which alleviate memory loss it must be demonstrated that CVT-E001 increases choline uptake in nervous tissue preparations.

Choline uptake has been examined in synaptosome preparations from whole brain and hippocampus in the presence of $Rb_1$, CVT-E001 and HC3. $Rb_1$ is a positive control as it has been previously demonstrated to increase choline uptake into synaptosomes whereas HC3 is a negative control which is known to inhibit choline uptake.

FIG. 1 demonstrates the effects of various doses of $Rb_1$ and HC3 on choline uptake by rat brain synaptosomes. This initial study indicates that our synaptosome preparations are viable, that $Rb_1$ promotes choline uptake and that HC3 inhibits choline uptake. The magnitude of these effects are consistent with the previous studies.

Experiments using both Rb1 and CVT-E001 indicate that both materials increase choline uptake into synaptosomes derived from the rat hippocampus (Table 2). CVT-E001 at a concentration approximating $1\times10^{-6}$ M saponins (molecular weight was established at 900) was always effective in promoting choline uptake. A higher dose ($1\times10^{-5}$ M) was not always effective. This observation is not unexpected as many pharmacological compounds have an optimal dose range and more or less of the material results in less biological activity.

TABLE 2

Effects of Rb1 and CVT-E001 on choline uptake into synaptosomes prepared from rat hippocampus

| Experiment Number | CVT-E001 $1 \times 10^{-6}$ M % control | Rb1 $1 \times 10^{-6}$ M % control |
|---|---|---|
| 1 | 123* | 126* |
| 2 | 113* | 111* |
| 3 | 121* | 125* |

Values are the mean percent increase in uptake of radioactive choline
*Significantly from controls p < 0.05 (ANOVA, Student/Newman/Kuels)

Table 3 demonstrates CVT-E001 and total ginsenosides (TS) and $Rb_1$ on choline uptake in rat brain synaptosomes. Since CVT-E001 only contains 8.1% $Rb_1$, 32.4% TS, the potency of CVT-E001 is significantly higher than either $Rb_1$ or TS.

TABLE 3

Comparison of Rb1, 100% of total ginsenosides (saponins, TS) and CVT-E001 on choline uptake in rat brain synaptosomes (% control).

Rb1: One of gensenosides isolated from American ginseng. >98% purity. Rb1-52, Rb1-53 and Rb1-54 represent 3 batches of Rb1.
TS: An extract of total ginsenosides isolated from American ginseng containing 25% Rb1, 19.4% Rc1 and 21.6% Rg1 + Re.
CVT-E001: An extract isolated from American ginseng containing 8.1% Rb1, 32.4% total ginsenosides

|        | 0.0011    | 0.011     | 0.11      | 1.1        | 11          |
|--------|-----------|-----------|-----------|------------|-------------|
| Rb1-52 | 108 ± 5.7 | 108 ± 4.4 | 108 ± 5.8 | 109 ± 5.4* | 111 ± 3.7*  |
| Rb1-53 | 106 ± 1.3 | 109 ± 3.6 | 108 ± 3.8 | 112 ± 4.8* | 114 ± 2.5** |
| Rb1-54 | 108 ± 3   | 110 ± 3.4 | 110 ± 2.6* | 112 ± 1.2* | 111 ± 2.6** |

|         | 0.0009    | 0.009     | 0.09      | 0.9        | 9           |
|---------|-----------|-----------|-----------|------------|-------------|
| TS      | 101 ± 1.7 | 104 ± 2.8 | 104 ± 3.2 | 106 ± 4.5  | 115 ± 5.9*  |
| CVT-E001| 106 ± 2.6 | 109 ± 5.8 | 113 ± 3.7 | 121 ± 1**  | 124 ± 2.6** |

Values represent mean ± SE. n = 4, *P < 0.05, ** P < 0.01 Student T test, compared to control Potency: CVT-E001 > TS > Rb1

The results show that both CVT-E001 and $Rb_1$ significantly stimulate choline uptake. However, CVT-E001 only contains 8.1% of $Rb_1$, yet shows similar even more potent effects at similar concentrations by weight. This indicates the synergistic effect of other substances to Rb1 in CVT-E001.

(2) Effect of 3 batches of CVT-E001 on MAO-A and MAO-B activity in rat brain in vitro.

TABLE 4

Effects of Several Ginseng Extracts on Monoamine Oxidase A (MAO-A) and Monoamine Oxidase B (MAO-B) Activity in vitro

| Extract Name   | Concentration | MAO-A % inhibition | MAO-B % inhibition |
|----------------|---------------|--------------------|--------------------|
| CVT-E001 Lot #1| 1 mg/ml       | 3.6 ± 2.1          | 5.5 ± 2.2          |
| CVT-E001 Lot #1| 10 mg/ml      | 38.4 ± 3.1         | 24.0 ± 4.2         |
| CVT-E001 Lot #3| 1 mg/ml       | 16.9 ± 3.1         | 18.4 ± 1.3         |
| CVT-E001 Lot #3| 10 mg/ml      | 66.9 ± 1.5         | 40.2 ± 2.2         |
| CVT-E001 Lot #4| 1 mg/ml       | 14.1 ± 2.5         | 22.3 ± 0.5         |
| CVT-E001 Lot #4| 10 mg/ml      | 68.2 ± 0.9         | 46.2 ± 1.8         |
| GLP            | 1 mg/ml       | 15.0 ± 1.0         | 28.6 ± 3.0         |
| GLP            | 10 mg/ml      | 51.2 ± 2.4         | 50.1 ± 1.2         |

Values are the mean±the standard error based on 5 (MAO-A) and 4 (MAO-B) determinations. In all cases a significant dose dependent effect was determined.
GLP=total essential oils, a portion of CVT-E001 containing substances between 24 and 35 minutes in HPLC-UV absorbance.

(3) Effect of CVT-E001 on learning using the Morris Water Maze and Scopolamine induced Amnesia Model.

Rationale

Ginsenosides including $Rb_1$ and $Rg_1$ have been demonstrated to enhance learning and memory. As CVT-E001 is a mixture of ginsenosides, it may not have the same properties as pure saponins. In order to claim that CVT-E001 can enhance learning and memory it must be demonstrated that this product can provide a measurable increase in task acquisition and/or retention in a scientifically accepted learning paradigm. The Morris water maze is a scientifically demonstrated procedure which can test spatial learning and memory. Rats are required to learn the location of a hidden platform in a murky swimming pool. If rats treated with CVT-E001 learn the location of a hidden platform faster than rats not treated with CVT-E001 them it is demonstrated that CVT-E001 enhances learning. The effects of CVT-E001 on memory can also be examined in scopolamine induced amnesia (scopolamine interferes with the cholinergic neurotransmitter system and impedes learning and memory). If CVT-E001 enhances learning and/or memory it should facilitate task acquisition and/or protect against memory loss in scopolamine treated animals.

Experimental Design

A study was designed of spatial learning and memory using the Morris water maze and scopolamine induced amnesia with CVT-E001 as the test compound. The specific aim of the experiment was to test if CVT-E001 affected the acquisition and/or retention of a new task in the presence of scopolamine induced amnesia. Rats (S/D strain males, 200–250 g, about 8 weeks old) are initially divided into two groups and fed either water (0.5 ml) or CVT-E001 (200 mg/kg/day in 0.5 ml water by gavage) for the duration of the experiment. Eight days after the initiation of CVT-E001 administration rats are given the task of learning the position of a platform hidden in a pool of murky water. The rats are placed in the pool 4 times per day for 5 days and the time required to find the platform in recorded (maximum duration 5 minutes). This time becomes shorter as the rats learn the task. On day 14 the two groups of rats are further subdivided into four groups. Six rats from each of the initial two groups receive saline injections while the remaining six rats from each initial group receive scopolamine (2 mg/kg) prior to being required to find the platform which has been moved to a new location (3 trials, maximum duration 3 minutes within 30 minutes of receiving either saline or scopolamine injection. On day 15 the procedure for day 14 was repeated with the platform remaining located in the position designated on day 14. On day 16, the procedure from day 14 was again followed except that the platform was moved to a location on the opposite side of the pool. On day 17 the procedure followed on day 14 was repeated except that the platform remains in the location designated on day 16. In each instance the time to locate the platform is recorded.

This experiment was repeated twice using 24 rats each time. The data from the two experiments was combined. One CVT-E001 treated rat died from accidental administration of CVT-E001 into the lungs. One control rat failed to find the platform on the last five trials of the learning curve. This data has been eliminated although it does not significantly affect the results. One CVT-E001 fed and scopolamine injected rat failed to find the platform on the final day and was excluded as a outlier.

Statistical analysis was by analysis of variance on log transformed data. As a posteriori test of significance were performed using the Newman-Keuls test.

Data from both individual trials and combined material from separate days is presented.

Results and Discussion

Figure 15:
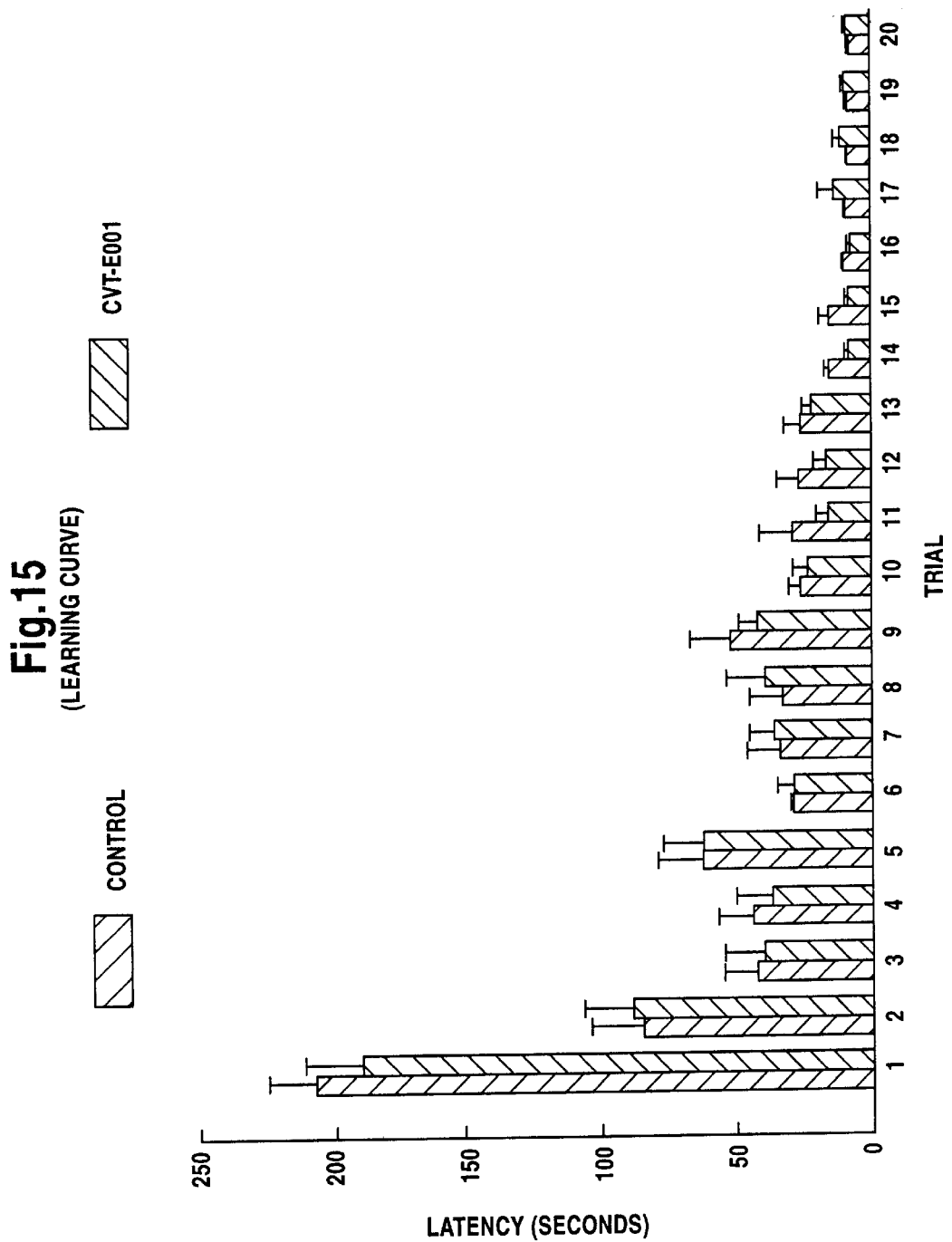
FIG. 15 shows the leaning curve of rats treated with CVT-E001 as measured by time to a platform.

Rats easily learned the task with the time to the platform dropping from about 200 seconds on the first trial to about 8 seconds on trial twenty (FIG. 15). The curve levels off at trial 14 when all animals have learned the task. On trials 5, 9 and 13 (the initial run of days 2, 3 and 4) there is a slight rebound effect indicating some loss of retained information overnight.

Figure 16:
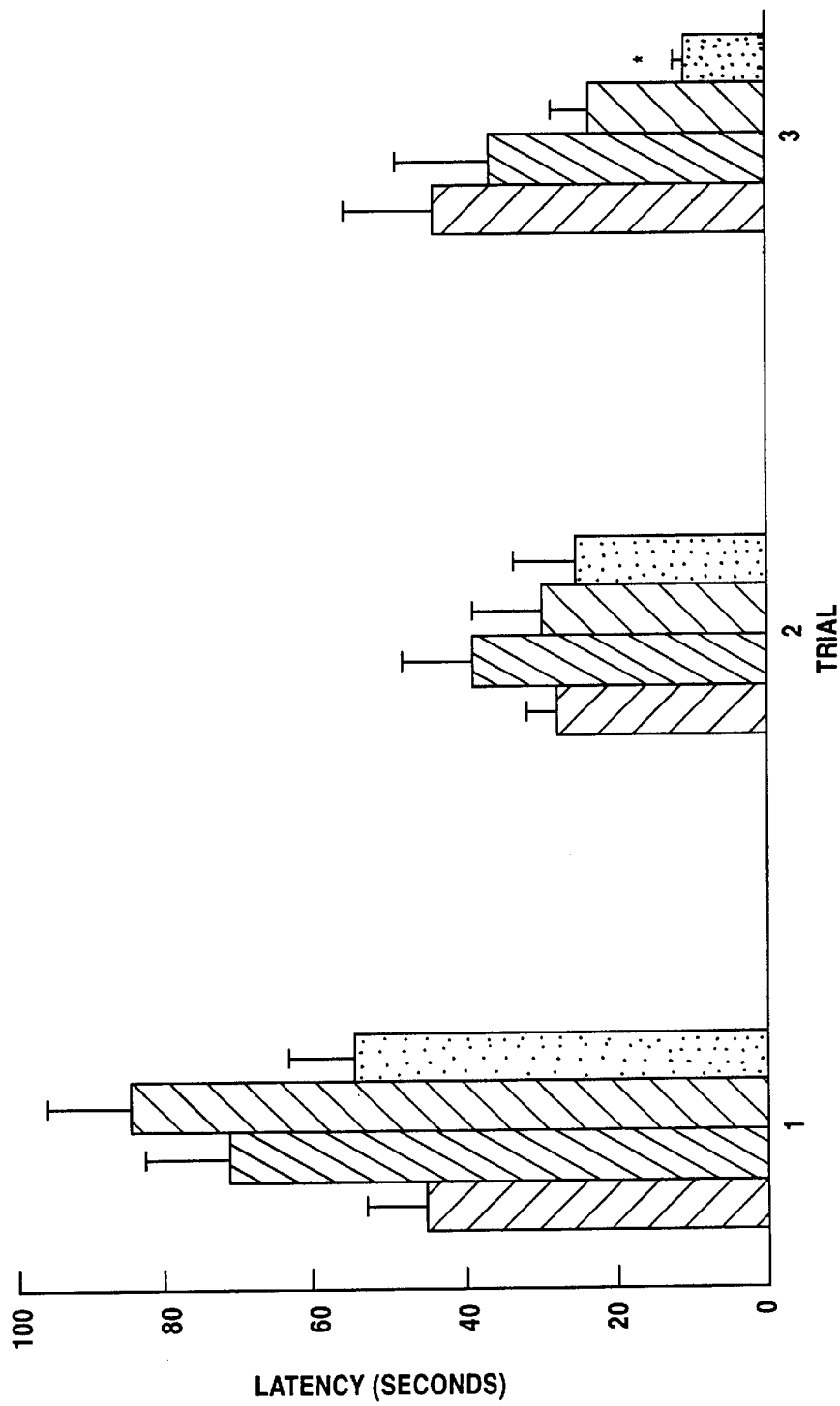
FIG. 16 shows the learning of a new task by rats treated with or without scopolamine and CVT-E001 on day 14 as measured by time to a platform.
Figure 17:
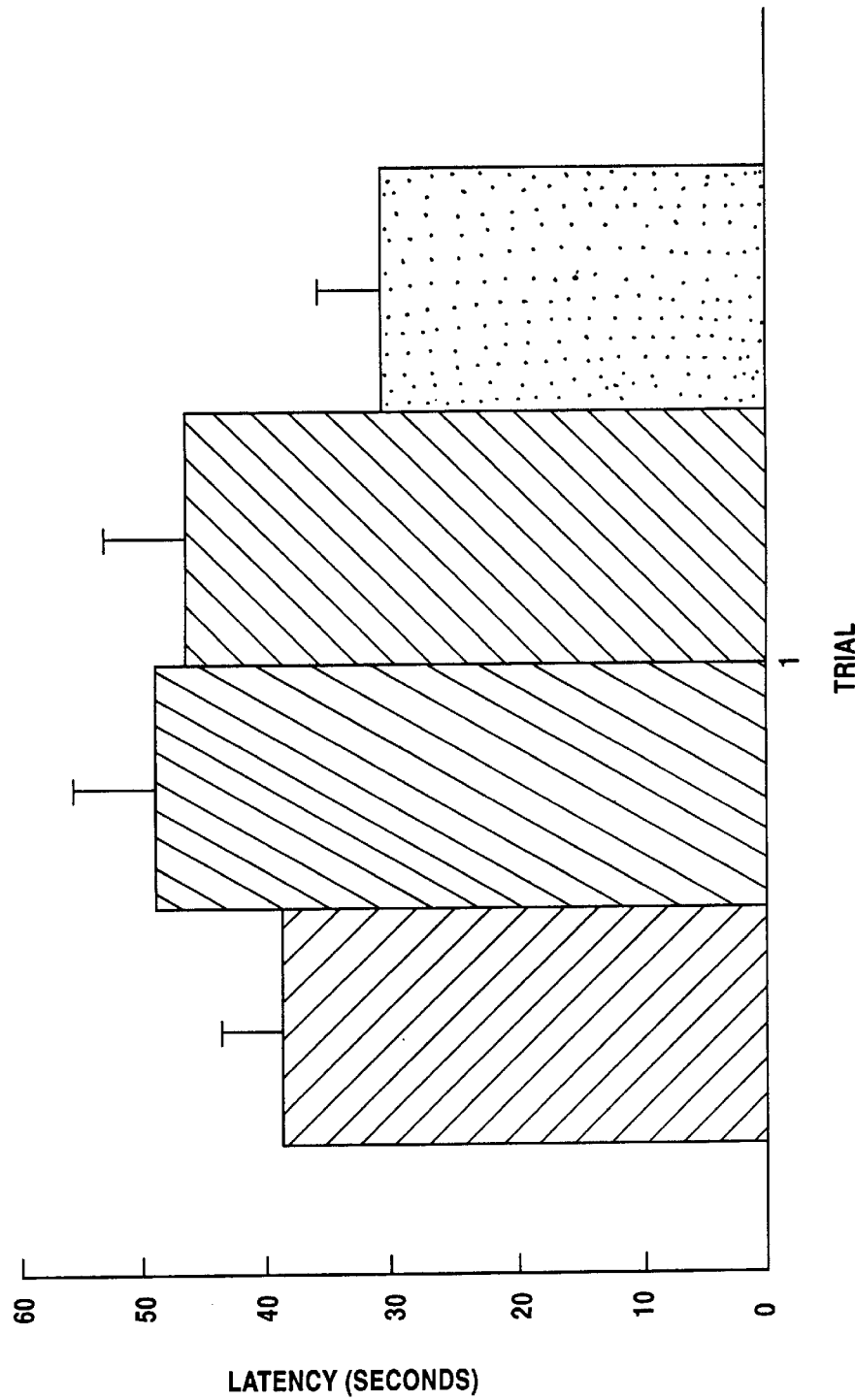
FIG. 17 shows the combined data of day 14.

When the rats were required to learn a new platform location in the presence or absence of scopolamine and CVT-E001 (FIG. 16), all treatments initially took the same length of time to locate the platform (FIG. 16, the first two trials). As this is a novel experience no difference should be seen. On the third trial, animals receiving CVT-E001 and saline were the only animals which outperformed the animals which had received scopolamine but no CVT-E001. When the data from this day is combined there is no evidence of a treatment effect (FIG. 17). This suggests that under these circumstances (initial short term acquisition with modest impairment of memory by scopolamine) CVT-E001 has no effect on information acquisition.

Figure 18:
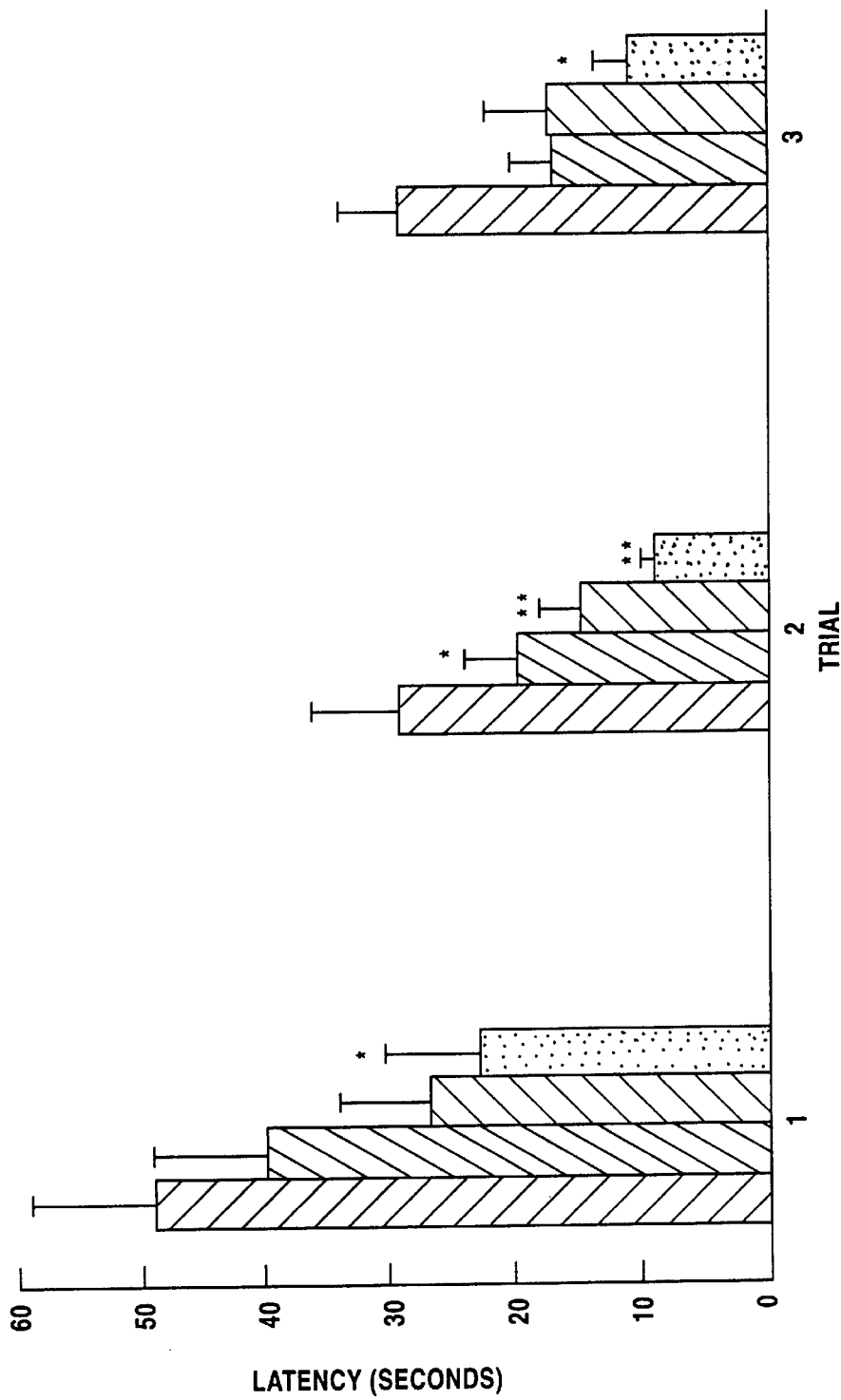
FIG. 18 shows the time to a platform of rats treated with or without scopolamine and CVT-E001 on day 15.

When the rats were asked to perform the same task on the following day (i.e. they were tested to see if they remembered the task from the previous day) rats which had received scopolamine but no CVT-E001 in all trials (FIG. 18). On trial 2, all treatment groups performed better than animals receiving scopolamine but no CVT-E001. When all trials from this day were combined (FIG. 19), animals receiving scopolamine but CVT-E001 had a significantly greater latency than all other groups indicating the presence of a scopolamine induced memory deficit that was offset by the presence of CVT-E001. As this test has a component which involves the recall of memory from the previous day, it indicates the CVT-E001 may prevent a deficit in long term memory integration rather than short term acquisition of information.

Figure 20:
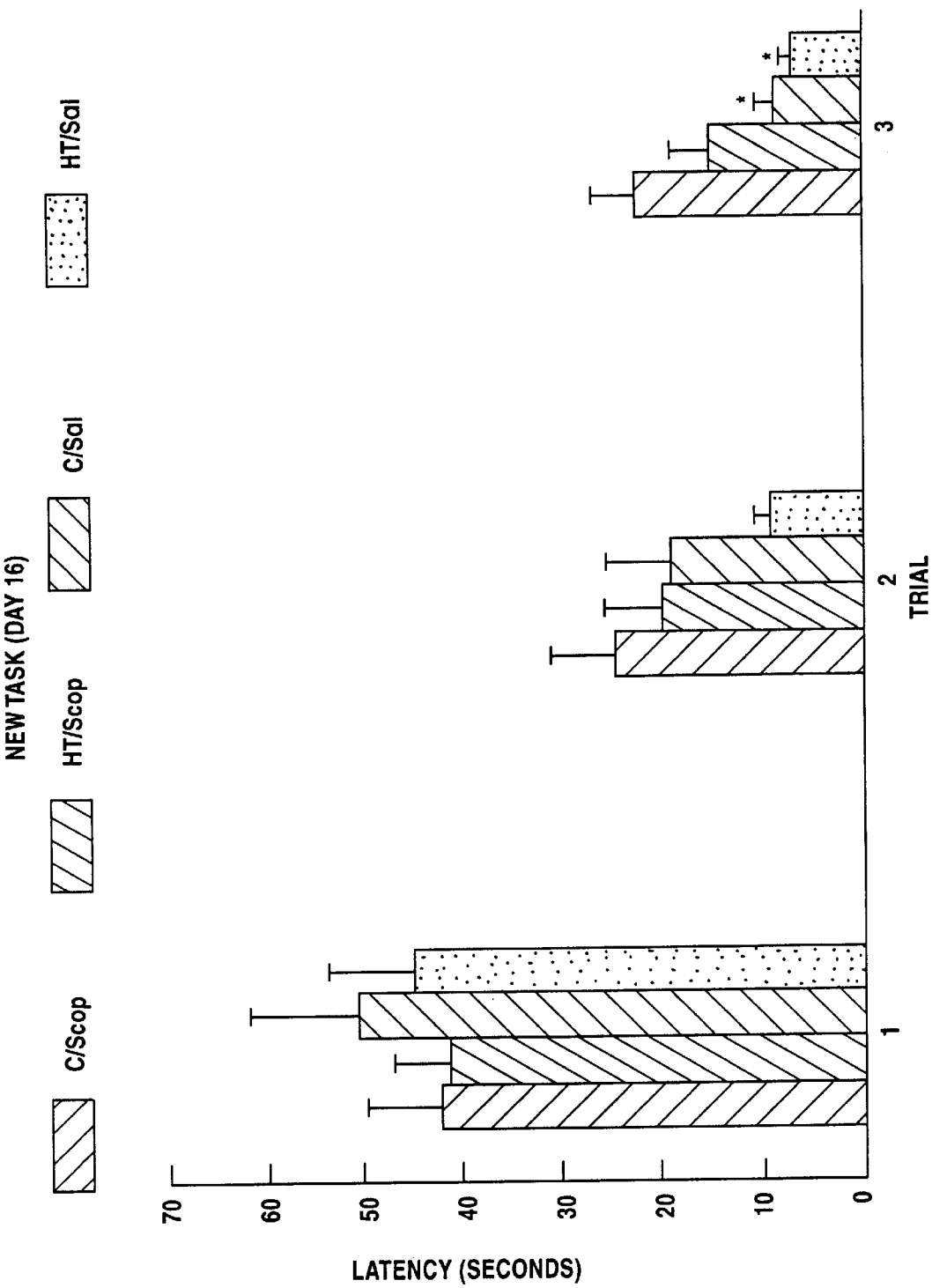
FIG. 20 shows the learning of a new task by rats treated with or without scopolamine and CVT-E001 on day 16 as measured by time to a platform.

When the rats were again asked to learn a new platform location there was no initial difference between treatment groups (FIG. 20, trial 1). However, by trial 3, the scopolamine treated animals demonstrated a scopolamine induced learning deficit. When the data from all trials from this day are combined there was no significant difference between treatment groups (FIG. 21) again indicating that CVT-E001 and modest scopolamine induced amnesia have little effect in the short term.

Figure 22:
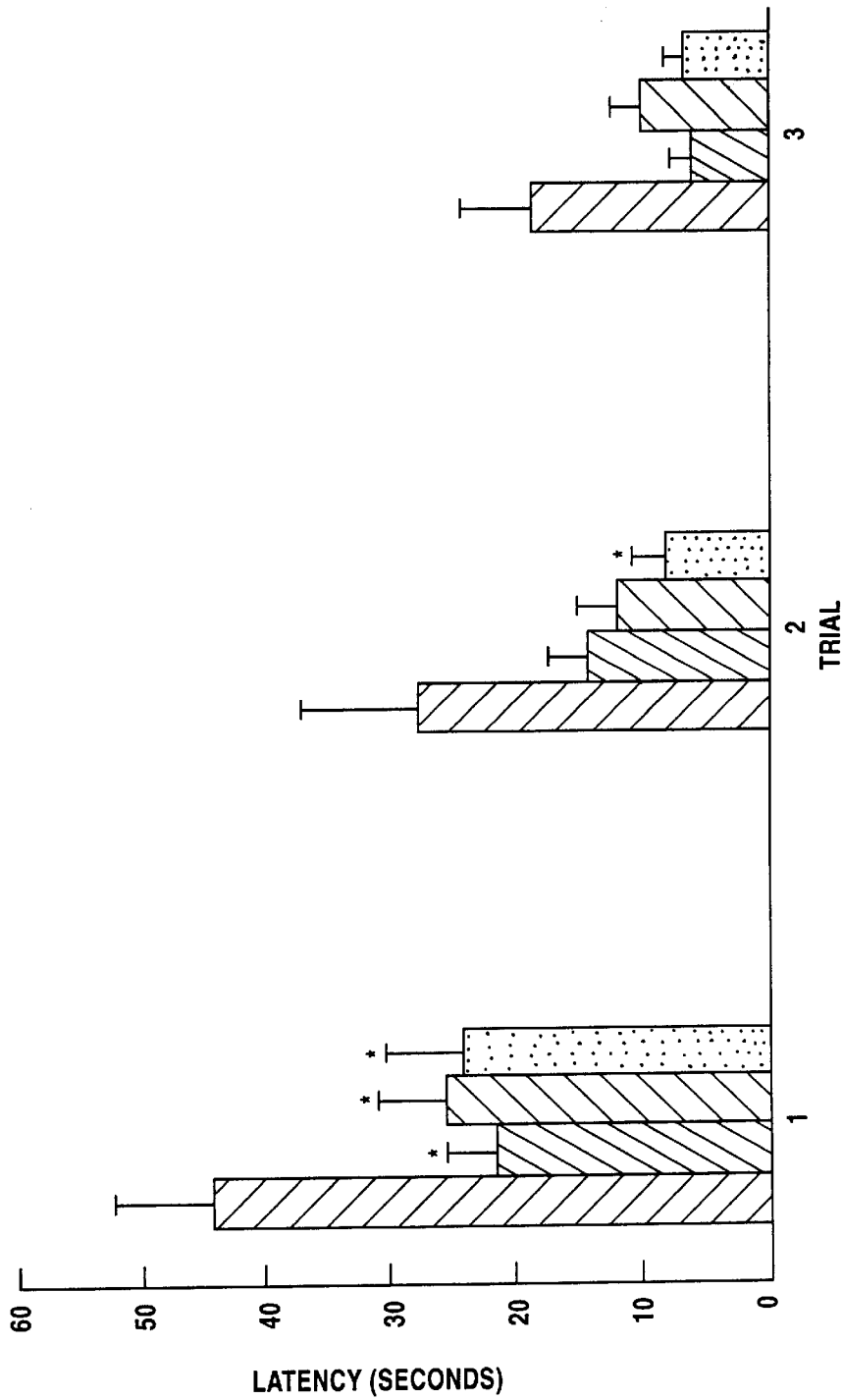
FIG. 22 shows the time-to-a-platform data when the rats were required to remember the final location of the platform on day 17.

When the rats were then required to remember the final location of the platform on the final day of the experiment, the scopolamine induced deficit was immediately obvious (FIG. 22). In the first trial animals which received scopolamine but no CVT-E001 were significantly impaired indicating a loss of long term memory. This amnesia was completely absent in animals which received both CVT-E001 and scopolamine and these animals performed the task as well as animals which did not receive scopolamine. When the data from all trials on this day are combined (FIG. 23) animals which receive scopolamine without pretreatment with CVT-E001 demonstrate a learning deficit. Animals which received CVT-E001 and scopolamine were not different from controls indicating the CVT-E001 completely abolished the learning deficit induced by scopolamine. Animals which received CVT-E001 but no scopolamine show no benefit when compared to animals which receive neither scopolamine or CVT-E001.

CVT-E001 is a mixture of ginsenosides which when provided as a dietary supplement to rats prevents scopolamine induced memory deficits. The effect is seen only in memory impaired animals as CVT-E001 does not appear to improve learning and memory in animals which do not have memory deficits. The effect of CVT-E001 does not appear to involve information acquisition and short term memory but rather long term memory integration since the greatest effects are demonstrated when animals are required to recall tasks 24 hours after learning them. As scopolamine is known to impair the cholinergic system, this work suggests that CVT-E001 can be of benefit to situations such as Alzheimer's disease where the cholinergic system is known to be impaired and spatial memory deficits occur.

(4) Memory Tests of CVT-E001 (Remember-FX) In Human Individuals

Methods:

Memory Quotient measurement tables were used. There were 5 tests.

A: Directed memory: After announcing 24 words, the examined was asked to repeat the words grouped by categories, e.g., vegetables.

B: Paired association memory: After announcing 12 pairs of words to the examined, and then repeating the first word of each paired words, the examined was asked to say the other paired words. Some pairs were related, such as UP-DOWN and SUN-MOON etc. Some were totally unrelated such as horse-lamp, etc.

C. Free recall of pictures: After showing 15 pictures, the examined was asked to recall what picture he or she had seen.

D. Recognition of meaningless figures: 20 figures of meaningless curves were shown to the examined first, followed by another 20 figures, half of which had been shown previously. The examined then was asked to point out which of the figures he or she had seen before.

E. Recall of the connections of portraits: Six portraits, each with a surname, a profession and a hobby, were shown to the examined: for example, the surname was Zhang, a teacher, hobby of watching TV. After a while, the portraits were shown again in a different order. The examined was asked to recall each portrait.

Each test was scored and the sum for each examined was calculated into Memory Quotient. Every examined was tested two times, before and after taking Remember-FX or control diet. Each examined was subjected to physical exams, one before and one after taking Remember-FX or control diet. The physical exams were to ensure no side effects of taking Remember-FX.

Young group: 10 university students, 5 female and 5 male, aged from 20 to 24, took Remember-FX two capsules daily (200 mg/capsule) for 13 days. The young control group consisted of 12 persons (9 male and 3 female). The aged group, from 46 to 64 years old, took Remember-FX 2 capsules daily for 14 days. The aged control group consisted of 5 people (3 male and 2 female), ages 40 to 65.

Statistics:

Group T-test was used for comparison between control group and experimental group.

Results:

Each test was scored and the sum of the score for each examined was calculated into MQ (memory quotient). Every examined was tested twice, once before and once after control diet or Remember-FX.

TABLE 5

MQS of young and aged group before and after taking Remember-FX

|   | Young | | Aged | |
| --- | --- | --- | --- | --- |
|   | Before | After | Before | After |
| 1 | 113.5 | 138 | 91 | 98 |
| 2 | 130 | 138 | 105 | 103.5 |
| 3 | 127 | 135 | 97.5 | 129 |
| 4 | 124 | 131 | 93 | 113 |
| 5 | 118 | 131.5 | 96 | 90 |
| 6 | 119 | 135 | 95 | 109 |
| 7 | 116 | 130 | 107 | 115 |
| 8 | 118 | 133 | 105 | 130 |
| 9 | 106 | 124 | 123 | 136 |
| 10 | 114 | 127 | 114 | 109 |

MQ is calculated by an equation from the scores and is divided into 7 grades. MQ>130 is first grade—above excellent; 129–120 is second grade—excellent; 119–110 good; 109–90 middle; 89–80 fair; 79–70 poor; 69–60 bad.

TABLE 6

Difference of MQ for young people

|   | Control | Remember-FX |
| --- | --- | --- |
| people | 12 | 10 |
| Test A | 3.8 ± 3.2 | 3.9 ± 3.1 |
| Test B | 1.9 ± 4.7 | 4.2 ± 3.8 |
| Test C | 3.2 ± 5.5 | 3.8 ± 5.1 |
| Test D | −3.0 ± 5.6 | 3.2 ± 3.3** |
| Test E | −0.7 ± 4.1 | 1.7 ± 2.9 |
| Sum | 5.3 ± 11.4 | 18.8 ± 7.4** |
| MQ | 3.7 ± 8.1 | 13.7 ± 5.3** |

Mean SD; *P<0.05, **P<0.01 in comparison with control. The values in Test A–E represent the difference of the scores before and after taking Remember-FX

TABLE 7

Difference of MQ for aged group

|   | Control | Remember-FX |
| --- | --- | --- |
| people | 5 | 10 |
| Test A | 2.6 ± 2.4 | 6.4 ± 5.0 |
| Test B | −0.3 ± 2.1 | 5.2 ± 3.6** |
| Test C | 2.8 ± 2.4 | −1.3 ± 5.0 |
| Test D | −7.3 ± 4.9 | 3.2 ± 3.7** |
| Test E | −4.8 ± 6.4 | −2.2 ± 5.9 |
| Sum | −6.6 ± 9.7 | 12.6 ± 15.3* |
| MQ | −5.6 ± 8.4 | 10.5 ± 12.8* |

Mean SD; *P<0.05, **P<0.01 in comparison with control. The values in Test A–E represent the difference of the scores before and after taking Remember-FX.

Conclusion:

(1) Table 51 shows that the 9 young examined increased their MQ except the second one. The fifth one increased by two grades. In the aged group, five people (3,4,7,8 and 9) showed an increase in grade. One of them (the 8th) increased by two grades. While there was one (10th) decreased by one grade, the other four (1,2,5 and 6) remained at the same grade (although there were slight variations).

(2) Table 6 and Table 7 suggested that there was a significant difference of MQS of the two groups between their corresponding controls. In the young age group, there was a difference in Test D and in aged group, there were differences in Test B and Test D. Test B is a test on language ability which is dominated by the left half of the cerebrum, while Test D is a drawing test, non-verbal, which is dominated by the right half of the cerebrum. The results suggested that Remember-FX might affect the left half of cerebrum predominately, while it affects the whole brain in the aged group.

Tests A and B tested the verbal (left) hemisphere of cerebrum, while Test D tested the right non-verbal hemisphere. Test C and E tested both hemispheres.

FIGURE CAPTIONS

FIG. 15. Learning curve of rats fed either water (0.5 ml) or CVT-E001 (200 mg/kg in 0.5 ml) per day (days 8–13). Rats were required to learn the location of a hidden platform at the center of the pool over a period of 5 days. Rats received 4 trials each day. Values are the mean±the standard error of the mean based on 35 or 36 trials. No significant treatment effects are demonstrated.

FIG. 16. Latency periods of rats learning the first new location of the hidden platform (day 14). Rats were divided into our groups. Group one (C/Scop) received only water as a dietary supplement and were injected with scopolamine (2 mg/kg) 15 minutes prior to the trials. Group 2 (HT/Scop) received CVT-E001 (200 mg/kg/day) as a dietary supplement and were injected with scopolamine (2 mg/kg) 15 minutes prior to the trials. Group 3 (C/Sal) received water as a dietary supplement and were injected with saline (0.2 ml) 15 minutes prior to the trials. Group 4 (HT/Sal) received CVT-E001 as a dietary supplement and were injected with saline (0.2 ml) 15 minutes prior to the trials.* Significantly different from C/Scop p<0.05.

FIG. 17. Combined data of three trials of latency periods of rats learning the first new location of the hidden platform (day 14). Treatments are the same as in FIG. 16. Values are the mean±the standard error of the mean based on 33 or 36 trials. No significant differences are demonstrated.

FIG. 18. Latency periods of rats remembering the first new location of the hidden platform (day 15). Treatments are the same as in FIG. 16. Values are the mean±the standard error of the mean based on 11 or 12 trials.* Significantly different from C/Scop p<0.05. **Significantly different from C/Scop p<0.01.

Figure 19:
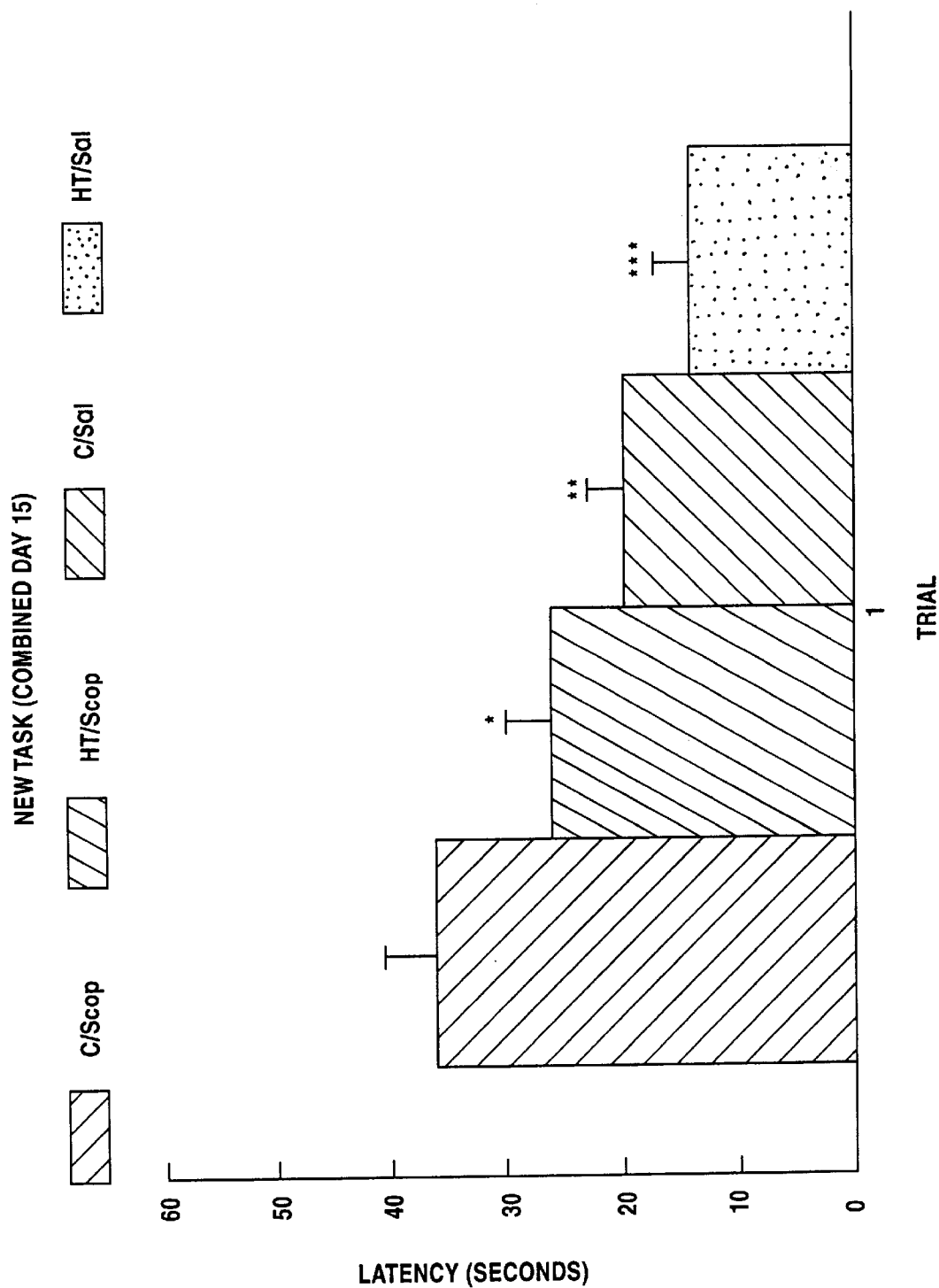
FIG. 19 shows the combined data of day 15.

FIG. 19. Combined data of three trials of latency periods of rats remembering the first new location of the hidden platform (day 15). Treatments are the same as in FIG. 16. Values are the mean±the standard error of the mean based on 33 or 36 trials* Significantly different from C/Scop p<0.05. Significantly different from C/Scop p<0.01. * Significantly different from C/Scop p<0.01 and HT/Scop p<0.05.

FIG. 20. Latency periods of rats learning the second new location of the hidden platform (day 16). Treatments are the same as in FIG. 16. Values are the mean±the standard error of the mean based on 11 or 12 trials. *Significantly different from C/Scop and HT/Scop p<0.01.

Figure 21:
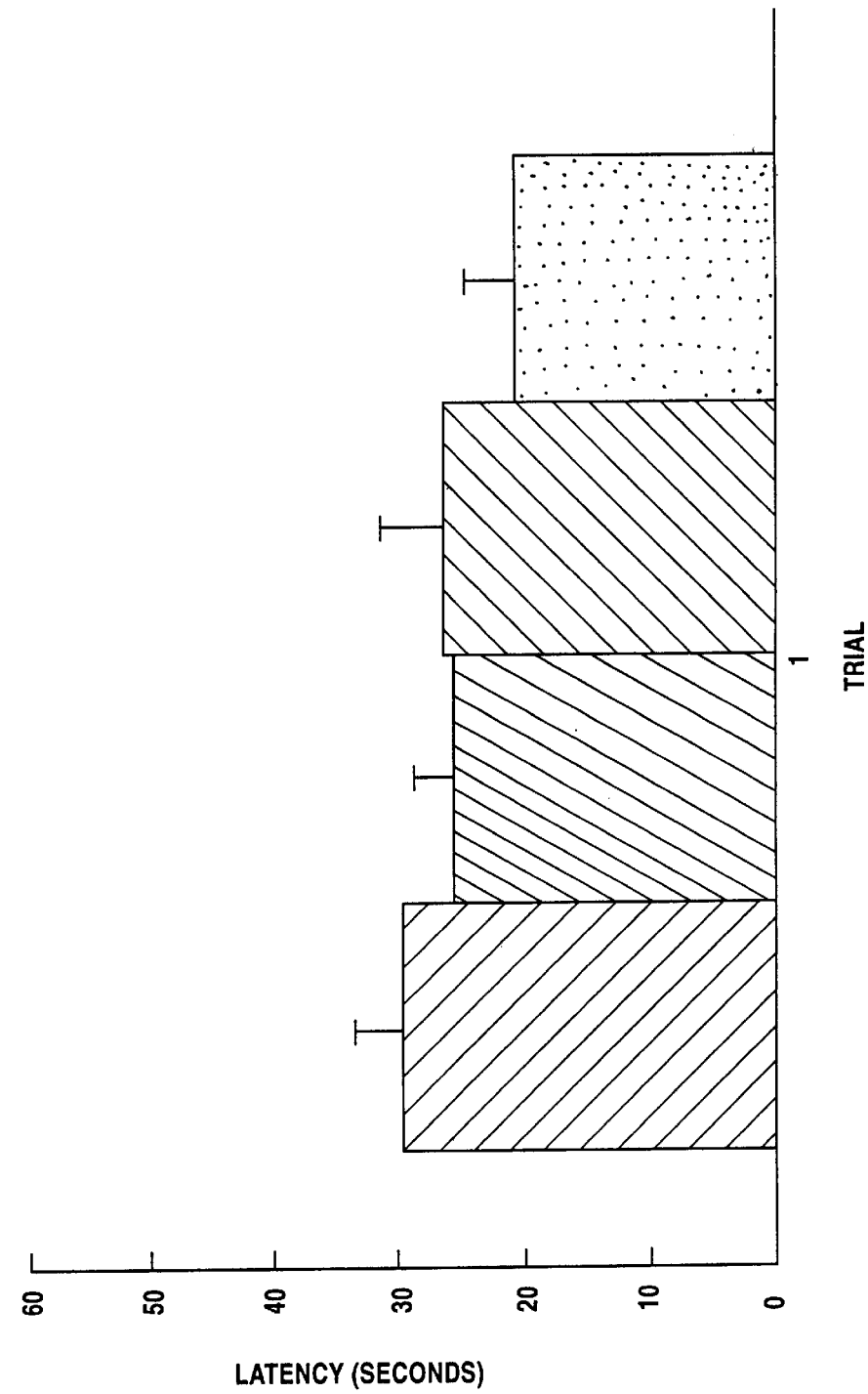
FIG. 21 shows the combined data of day 16.

FIG. 21. Combined data of three trials of latency periods of rats learning the second new location of the hidden platform (day 16). Treatments are the same as in FIG. 16. Values are the mean±the standard error of the mean based on 33 or 36 trials. No significant differences are demonstrated.

FIG. 22. Latency periods of rats remembering the second new location of the hidden platform (day 17). Treatments are the same as in FIG. 16. Values are the mean±the standard error or the mean based on 11 to 12 trials. *Significantly different from C/Scop p<0.05.

Figure 23:
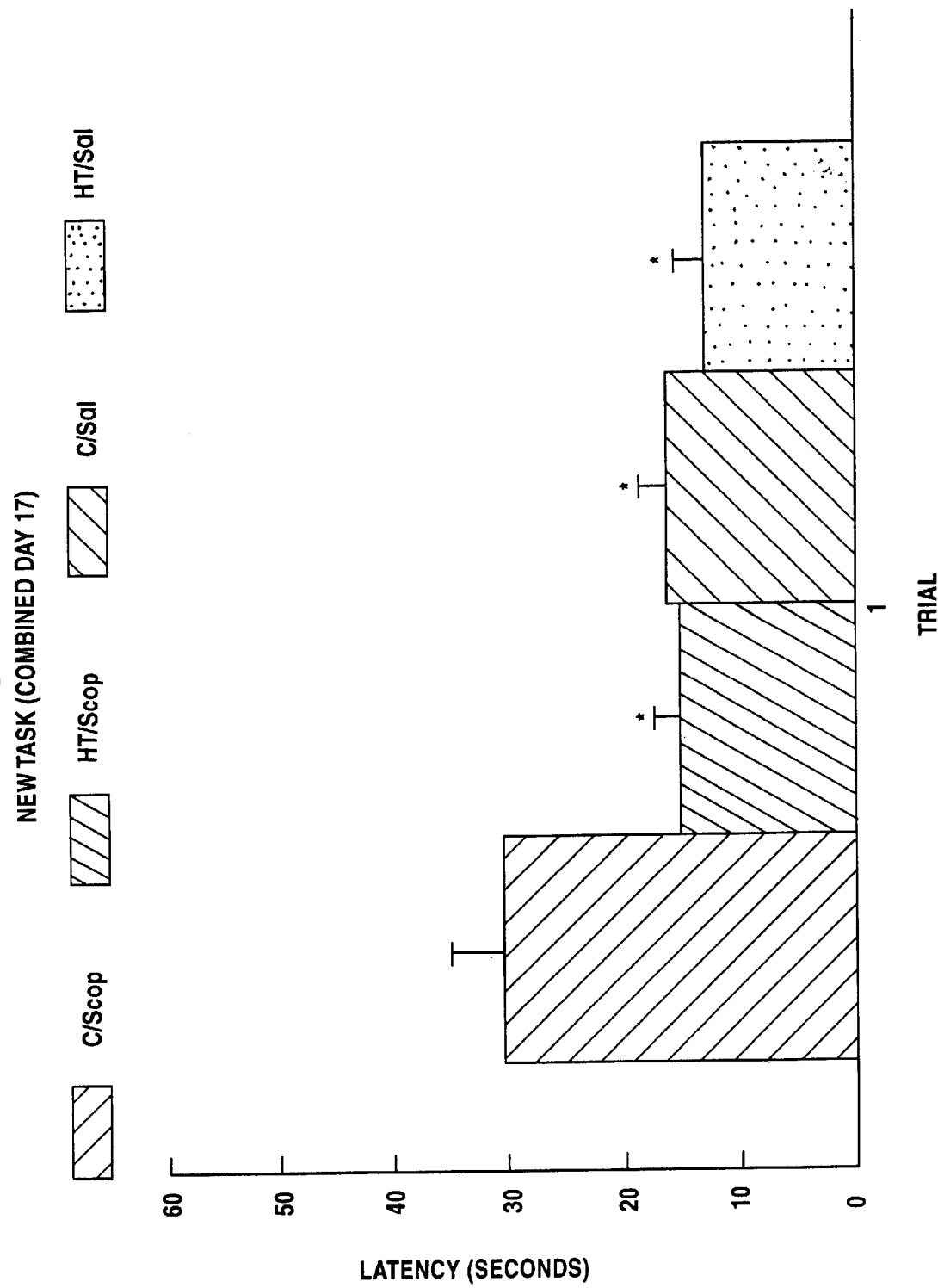
FIG. 23 shows the combined data of day 17.
Figure 24:
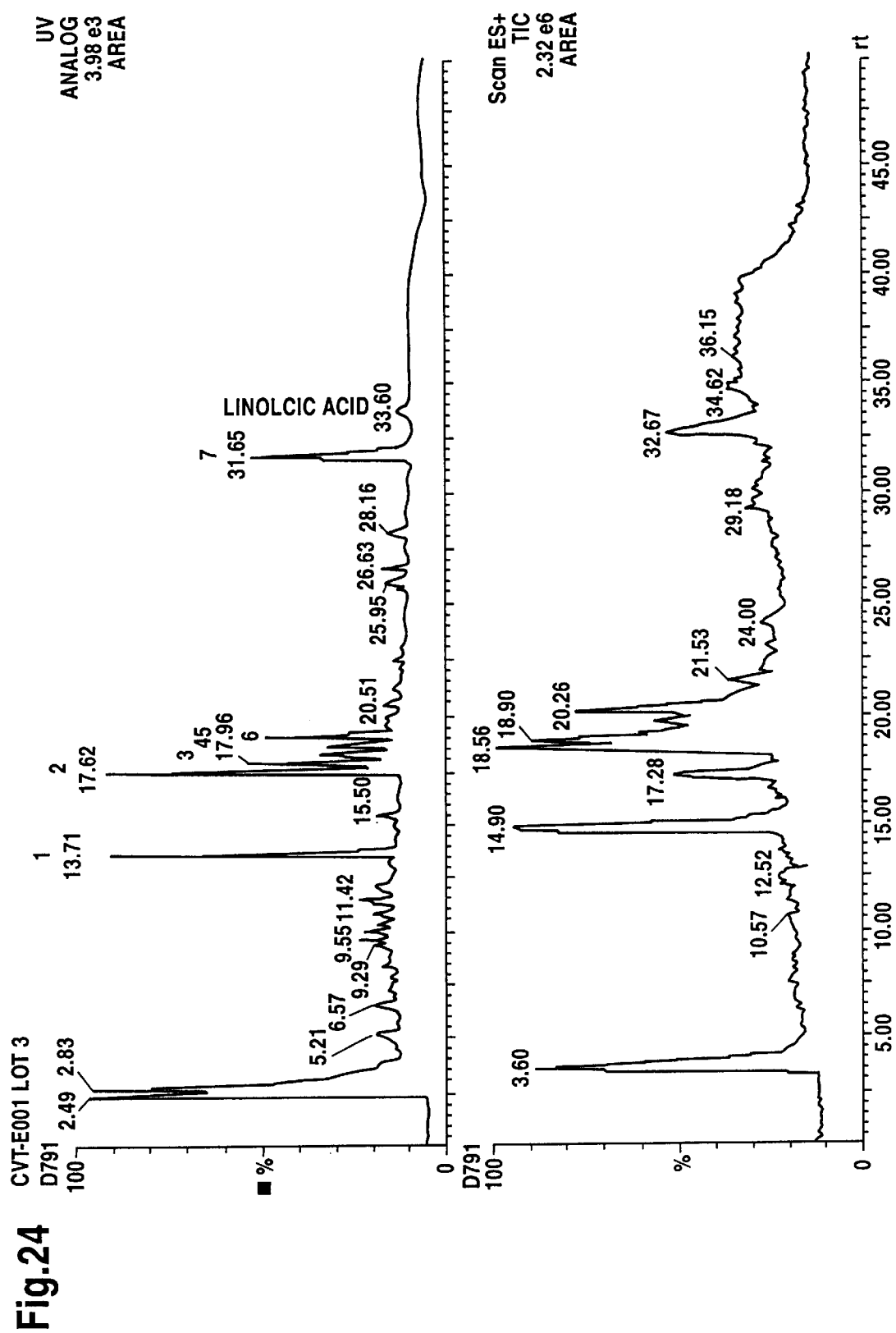
FIG. 24 provides ultraviolet absorbance characteristics (uv ANALOG) and total ion counts (TIC) for lot 3 of CVT-E001.

FIG. 23. Combined data of three trials of latency periods of rats remembering the second new location of the hidden platform (day 17). Treatments are the same as in FIG. 16. Values are the mean±the standard error of the mean based on 33 or 36 trials. *Significantly different from C/Scop p<0.01.

Stimulation of Neurite outgrowth by HT-1001

In vitro cultures of PC12 and neuroblastoma NIE-115 cell lines Introduction.

We have discovered a new mechanism of action of HT-1001, which is the stimulation of neurite outgrowth in PC12 (pheochromocytoma) cell lines. This result indicates that HT-1001 not only acts to alleviate symptoms, but also alters the progression of neurodegenerative diseases. The beneficial effects (prevention/treatment) of HT-1001 may apply to degenerative diseases such as senile dementia, Parkinson's, multi-infarct dementia etc.

Ginsenosides have been reported to have a number of actions on the central nervous system. These include CNS stimulation or depression, anticonvulsant activity, antipsychotic activity, analgesic activity, anti-fatigue and anti-stress activity, and improved performance in various memory tasks, (Takagi K et al *Japan J Pharmacol* 22: 339 (1972), Saito H and Nabata H *Japan J Pharmacol* 22:245 (1972), Saito H et al *Japan J Pharmacol* 23:43 (1973), Takagi et al *Japan J Pharmacol* 24: 41 (1974), Saito et al *Japan J Pharmacol* 24: 119 (1974), Saito H *Japan J Pharmacol* 27:509 (1977), Hong S A *Korean J Pharmacol* 10:1 (1974)). It is known that pure ginsenosides Rb1 and Rg1 can improve memory in experimental animals (Saito H in *Advances in Chinese Medicinal Materials Research*, ed. Chang H M et al *World Sci Publ.* Singapore, 1985, p 509, Saito H in *Recent Advances in Ginseng Studies*, ed Shibata S Hirokawa Publ. Co. Tokyo 1990, p 99, Benishin C G et al *Pharmacology* 42:223 (1991)) and its mechanism of action on cholinergical neurotransmission in the brain is well defined. In addition to the behavioral effect which have been described to Rb/Rg1, ginsenosides Rb1 and Rd (another ginsenoside) were found to enhance neurite outgrowth of dorsal and sympathetic ganglia by Nerve Growth Factor (NGF) (Saito H in *Advances in Chinese Medicinal Materials Research* ed. Chang H M et at *World Sci Publ.* Singapore, 1985, p 509), but had no effect on its own. Until now very little information has appeared on the cellular mechanism of this enhancement. To date, no studies have been published on the action of Rb1 or any other ginsenoside on neurite outgrowth. A recent report has demonstrated that a "lipophilic" extract of ginseng also possesses neurotrophic activity (Mohri T et al *Planta Med* 58: 321 (1992)), however the active constitute of this extract remains to be elucidated.

NGF was first discovered in the 1950s and is the prototype neurotrophin. NGF has many actions which are associated with the development and maintenance of neuronal pathways. As well, the biological actions have been reviewed (Levi-Montalcini R *Science* 237: 1154 (1987), Levi A and Alema S *Ann Rev Pharmacol Toxicol* 31:205 (1991)). Peripheral NGF is essential for the survival of adrenergic sympathetic and primary sensory neurons during development. It influences the growth and nueronal circuitry of somatosensory fibers during developement (Hefti F et al *Neurobiol Aging* 10: 75 (1989)) and after injury in adults (Raivich G and Kreutzberg G W *Int J Devel Neurosci* 11:311, 1993)). In the brain, NGF promotes the survival of basal forebrain cholinergic neurons (Martin et al *J. Cell Biol* 106: 829 (1988), Mobley W C et al *Mol Brain Res* 1:53 (1986)) and prevents the loss of these same neurons following injury (Hagg T et al *Brain Res* 505: 29 (1989)), Tuszynski M H et al *Ann Neurol* 30: 625 (1991)). NGF has also been reported to promote differentiation of neuronal precursor cells (Hartikka J and Hefti F *J Neurosci Res* 21:352 (1988)). PC12 cells respond to NGF treatment by neurite outgrowth and electrical excitability (Green L A et al *Adv Cell Neurobiol* 3: 373 (1982)) as well as other properties. Currently the design and development of neurotrophic factors for the treatment of various degenerative diseases are actively being pursued (Hefti F *J Neurobiol* 25: 1418 (1994), Tonnaer J A D M and Dekker A J A M *In Anti-Dementia Agents* Academic Press 1994, p 139).

Alzheimer's Disease (AD) is associated with degeneration of cholinergic nerve tracts including projections from the basal forebrain to the cortex and hippocampus. The PC12 cell line (Greene L A and Tischler A S *Adv Cell Nuerol* 3: 373 (1982)) is one of the models for the study of the functions of these nerve tracts. The cell line is phenotypically a chromaffin cell line, but can be induced to express adrenergic (Greene L A and Tischler A S *Proc Nat Acad Sci USA* 73:2424 (1976), Aloe L and Levi-Montalcini R *Proc Nat Acad Sci USA* 76: 1246 (1979)) and cholinergic markers as well (Greene L A and Rein G *Brain Res* 138: 521 (1977), Ritchie A K *J Physiol* (Lond) 286: 541 (1979), Schubert D et al *Proc Nat Acad Sci USA* 74: 2579 (1977), Jumblatt J E and Tischler A S *Nature* 297: 152 (1982)). This model has the advantage that (Shibata S et al *Economic and Medicinal Plant Res* 1:217 (1985)) it is an immortalized cell line, (Saito H in *Advances in Chinese Medicinal Materials Research*, ed Chang H M et al *World Sci Publ.* Singapore, 1985, p 509) it is sensitive to, but not dependent upon NGF for survival, and (Saito H in *Recent Advances in Ginseng Studies.* ed Shibata S Hirokawa Publ Co. Tokyo 1990, p 99.) it shares many properties in common with central cholinergical neurons of the basal forebrain. It has been noted that PC12 cells are not sensitive to all of the trophic factors that central cholinergical neurons respond to, while the central cholinergical neuron respond to all trophic factors that PC12 cells respond to. For this reason the PC12 cell line can be viewed as an ideal model system which will likely not give any false positive results, but may give false negative results, i.e., it may be possible to miss a trophic factor which is acting on a central cholinergical neuron.

PC12 cells have been reported to respond to NGF in many ways, including, but not limited to, the following: development of membrane excitability, synthesis, assembly and stabilization of cytoskeletal structure, increased cell adhesion, hypertrophy and increased anabolic activity, decreased DNA synthesis and cellular proliferation (Werrback-Perez K et al *Prog Brain Res* 86: 183 (1990); selective induction of antioxidant (e.g. catalase) and energy metabolism enzymes (Perez-Polo J R and Werbach-Perez K in *Recent Achievements in Restorative Neurology* 30: 321 (1985), Perez-Polo J R and Werbach-Perez K in *Neural Development and Regeneration* Sringer-Verlag, Heidelberg, p 339 (1987), Perez-Polo J R and Werbach-Perez K *Nervous*

*System regeneration* Alan Liss New York p 201 (1988); stimulation of cholinergic neurotransmitter metabolism (e.g. CHAT activity, (Greene L A and Rein G *Brain Res* 138: 521 (1977), Ritchie A K *J Physiol* (Lond) 286: 541 (1979), Schubert D et al *Proc Nat Acad Sci USA* 74: 2579 (1977), Jumblatt J E and Tischler A S *Nature* 297: 152 (1982); altered gene expression (Szeberenyi J and Erhardt P *Biochim Biophys Acta* 1222: 187 (1994); increased neurite outgrowth (Greene L A and Tischler A S *Proc Nat Acad Sci USA* 73:2424 (1976), increased expression of surface membrane receptors (Green L A and Tischler A S *Adv Cell Neurol* 3: 373 (1982); increased expression of APP-695 (which is important with respect to the etiology of Alzheimer's Diseases, (Schubert D et at *Neuron* 3: 689 (1989)); increased expression of omega-CgTx sensitive Ca2+ channels (Usowicz M M et al *J Physiol* (Lond) 426: 95 (1990)); increased expression of zeta-PKC, and down-regulation of other isoforms of PCK leading to enhancement of neurite outgrowth (Colemen E S and Wooten M W *J Mol Neurosci* 5: 39 (1994). Because PC12 cells respond to NGF with a variety of documented responses, they are a likely candidate for studying the NGF-like properties of other substances. There is support for the notion that these cells are a good model for central cholinergical neurons of the basal forebrain.

Neuroblastoma NIE-115 are undifferentiated murine neuroblastomas which have been useful for the study of neuronotrophic activities.

Material and Method:

PC12 cells were seeded and maintained in 100 $cm^2$ tissue culture dishes at 37° C. in RRMI1640 containing 1% antibiotics, 10% heated inactivated horse serum and 5% fetal bovine serum in a water saturated atmosphere of 95% air and 5% $CO_2$. NIE-115 cells were maintained in a flask in 90% DMEM (Dulbecco's Modified Eagle Medium, Gibco, Grand Island, N.Y., USA) with 10% FBS and antibiotic PNS (penicillin, neomycin streptomycin). The culture plates were maintained in a temperature-controlled (37° C.) humidified atmosphere consisting of 95% room air and 5% $CO_2$. The cells were mechanically dislodged for the experiment by forceful aspiration of the medium through a Pasteur pipette and plated in 35 mm collagen-coated tissue culture dishes containing a total of 2.0 ml of complete medium at a density of $1 \times 10^4$ cells/ml. The medium was changed 3 times per week.

The cellular response to Nerve Growth Factor (NGF) and samples were determined by counting the number of cells contained processes in PC12 cells. Photographs of the cells were taken after seven and 14 days of treatment. Two fields were chosen in every dish before the films were developed and printed.

The cells and neurites were counted as follows.

Cells with circular or global shapes and no neurite outgrowth were scored as 0 (S0).

Cells which became elongated or showed short neurite outgrowth were scored as S1.

Cells with more than two small neurites on the cell bodies were scored as S2.

Cells with one or two neurites with the length of at least two times diameter as their body were scored as S3.

Cells with more than two long neurites were scored as S4.

The neurite index was calculated as below:

Neurite index (In)=total neurite score ($\Sigma S$)/total cell number ($\Sigma N$)

$\Sigma S = S1*N+S2*N+S3*N+S4*N$; N is the cell number of every cell field.

Experimental Results:
1. NGF increased neurite outgrowth in PC12 in a dose-dependent manner seven days after treatment (FIG. 26).
2. HT-1001 increased neurite outgrowth in PC12 in a dose-dependent manner seven days after treatment (FIG. 27).
3. HT-1001 increased neurite outgrowth in NIE-115 in a dose-dependent manner seven days after treatment (FIG. 28). FIG. 29 and FIG. 30 show the original photos of control and treated cells respectively. Little or no neurite outgrowth was observed in the control group while significant neurites were found in treated cells.

Conclusion:

HT-1001 caused a NGF-like effect in stimulating neurite outgrowth in both PC12 and NIE-115 cell lines. This may contribute to its beneficial effect in the treatment and prevention of neurodegenerative diseases.

What is claimed is:

1. A method of obtaining a reproducible extraction process for use as a standard process for extracting a pharmacologically active mixture of chemical components from a plant, the method comprising:
    (a) extracting a plurality of pharmacologically active mixtures of chemical components from a plant in a plurality of different extraction processes, to produce a plurality of extracts;
    (b) obtaining a biological fingerprint of the pharmacological activity of each extract from step (a) by conducting at least two in vitro and at least two in vivo pharmacological tests on each extract, wherein each of the tests is known to correlate with effective treatment of a medical condition in a patient;
    (c) choosing the one of the plurality of extracts which displays the best pharmacological activity in step (b);
    (d) repeating, at least once, the extraction process used to produce the chosen extract of step (c), to produce at least one test extract;
    (e) (1) obtaining chemical fingerprints of the chosen extract and the at least one test extract by distinguishing the identify and amount, relative to each other, of the chemical components in the pharmacologically active mixture of each extract, and
    (2) repeating said obtaining step (b) using the at least one test extract; and
    (f) comparing the chemical fingerprints and the biological fingerprints of the chosen extract and the at least one test extract, wherein
        when the chemical components of the at least one test extract are present in an amount which is at most 10% more or less than the amount of the same chemical component of the chosen extract, and
        when each pharmacological test result of the at least one test extract is at most 10% more or less than the corresponding pharmacological test result of the chosen extract,
    then the extraction process used to produce the chosen extract is selected as the standard process for extracting the pharmacologically active mixture of chemical components from the plant.

2. A method of obtaining reproducible and high pharmacological activity from a pharmacologically active mixture of chemical components derived from a plant source, comprising:
    (a) conducting a plurality of different extraction processes on a plurality of samples from the same plant source to produce a plurality of plant extracts;
    (b) conducting at least one pharmacological test known to correlate with a changed biological state of a living organism on each plant extract;

(c) selecting the plant extract displaying the highest pharmacological activity in step (b);

(d) repeating the extraction process used to produce the selected extract of step (c) to produce a test extract;

(e) obtaining chemical fingerprints providing at least qualitative information regarding chemical components of both the selected extract and the test extract;

(f) repeating the tests of step (b) on the test extract;

(g) comparing the chemical fingerprints and the pharmacological activity of the selected extract and the text extract, such that when the chemical component(s) of the test extract are present in an amount which differs no more than about + or 31 10% that of the corresponding pharmacological test activity of the selected extract, then that extraction process used to produce the selected extract is chosen as the standard process for extracting the pharmacologically active mixture of chemical components from the plant source.

3. The method of claim 2 wherein the at least on pharmacological test is at least one of an in vitro and an in vivo pharmacological test.

4. The method of claim 2 wherein the at least one pharmacological test is at least two in vitro and at least two in vivo pharmacological tests.

5. The method of claim 2 wherein the changed biological state of a living organism is an effective treatment of a medical condition in a patient.

6. The method of claim 2 wherein the at lest qualitative information includes qualitative and quantitative information.

7. The method of claim 2 wherein the patient is a human.

8. A method of obtaining a pharmacologically active mixture of chemical components having a reproducibly high pharmacological activity derived from a plant source comprising, (a) conducting a plurality of different extraction processes on a plurality of samples from the same plant source to produce a plurality of plant extracts;

(b) conducting at least two in vitro and at least two in vivo pharmacological tests known to correlate with effective treatment of a medical condition in a patient on each plant extract;

(c) selecting the plant extraction displaying the highest pharmacological activity in step (b);

(d) repeating the extraction process used to produce the selected extract of step (c) to produce a test extract;

(e) obtaining chemical fingerprints providing at least one of qualitative and quantitative information regarding chemical components of both the selected extract and the test extract;

(f) repeating the tests of step (b) on the test extract;

(g) comparing the chemical fingerprints and the biological activity of the selected extract and the test extract, such that when the chemical component(s) of the test extract are present in an amount which differs no more than about 30 or −10% that of the corresponding pharmacological test activity of the selected extract, then that extraction process used to produce the selected extract is chosen as the standard process for extracting the pharmacologically active mixture of chemical components having a reproducibly high pharmacological activity.

* * * * *